US010478616B2

(12) United States Patent
Montgomery, Jr. et al.

(10) Patent No.: US 10,478,616 B2
(45) Date of Patent: Nov. 19, 2019

(54) METHOD AND SYSTEM FOR PHYSIOLOGICAL TARGET LOCALIZATION FROM MACROELECTRODE RECORDINGS AND MONITORING SPINAL CORD FUNCTION

(71) Applicant: Greenville Neuromodulation Center, Greenville, PA (US)

(72) Inventors: Erwin B. Montgomery, Jr., Middleton, WI (US); He Huang, Seven Fields, PA (US)

(73) Assignee: Greenville Neuromodulation Center, Greenville, PA (US)

(*) Notice: Subject to any disclaimer, the term of this patent is extended or adjusted under 35 U.S.C. 154(b) by 914 days.

(21) Appl. No.: 14/831,495

(22) Filed: Aug. 20, 2015

(65) Prior Publication Data

US 2016/0051812 A1 Feb. 25, 2016

Related U.S. Application Data

(60) Provisional application No. 62/039,559, filed on Aug. 20, 2014.

(51) Int. Cl.
*A61N 1/05* (2006.01)
*A61B 5/0492* (2006.01)
(Continued)

(52) U.S. Cl.
CPC .......... *A61N 1/0534* (2013.01); *A61B 5/0484* (2013.01); *A61B 5/0488* (2013.01);
(Continued)

(58) Field of Classification Search
None
See application file for complete search history.

(56) References Cited

U.S. PATENT DOCUMENTS 7,136,696 B2 11/2006 Montgomery, Jr.
7,181,288 B1 * 2/2007 Rezai ................... A61N 1/0529
607/116
(Continued)

FOREIGN PATENT DOCUMENTS

WO 2014055328 A1 4/2014

OTHER PUBLICATIONS

Dinner et al., EEG and evoked potential recording from the subthalamic nucleus for deep brain stimulation of intractable epilepsy, Clinical Neurophysiology, 2002, pp. 1391-1402, vol. 113, No. 9, Elsevier Science Ireland Ltd., Cleveland, OH.
(Continued)

*Primary Examiner* — Matthew Kremer
(74) *Attorney, Agent, or Firm* — The Webb Law Firm

(57) ABSTRACT

Provided herein are a method and system are provided for the localization of clinically relevant electrophysiological signals necessary for the proper placement of the electrodes for nervous system stimulation. The system provides electrical and mechanical means to stimulate or excite neural structures in order to elicit specific neural responses. The method can include mechanical vibratory stimulation, cutaneous electrical stimulation, electrical stimulation of the peripheral nerves, or photic stimulation, and recording of local field potentials and extracting evoked potentials in response to stimulation. The method also includes extracting components of the evoked potentials that relate the signal in the evoked potentials to specific anatomical structures and localization of the source of the evoked potentials recorded so as to identify the location of the source relative to the recording electrode with high resolution by sampling the evoked potentials with a relative large (macro) electrode that is moved in small incremental steps.

17 Claims, 13 Drawing Sheets

(51) Int. Cl.
A61B 5/00 (2006.01)
A61B 5/0484 (2006.01)
A61B 5/0488 (2006.01)

(52) U.S. Cl.
CPC ............ *A61B 5/0492* (2013.01); *A61B 5/407* (2013.01); *A61B 5/4064* (2013.01)

(56) References Cited

U.S. PATENT DOCUMENTS

| | | | |
|---|---|---|---|
| 7,957,793 B2 | 6/2011 | Montgomery, Jr. et al. | |
| 8,150,795 B2 | 4/2012 | Montgomery, Jr. et al. | |
| 2010/0016732 A1* | 1/2010 | Wells | A61B 5/0059 600/476 |
| 2014/0296737 A1* | 10/2014 | Parker | A61B 5/04001 600/554 |

OTHER PUBLICATIONS

Floeter et al., Cutaneous withdrawal reflexes of the upper extremity, Muscle Nerve 1988, pp. 591-598, vol. 21, No. 5, Institute of Health, ethesda, MD.

Floyd et al., Deconvolution of Compton Scatter in SPECT, J Nucl. Med. 1985, pp. 403-408, vol. 26, No. 4, Department of Radiology, Duke University Medical Center, Durham, North Carolina.

Fokas et al., Reconstruction algorithm for single photon emission computed tomography and its numerical implementation, J. R. Soc. Interface 2006, pp. 45-54, vol. 3, No. 6, Department of Applied Mathematics and Theoretical Physics, University of Cambridge, Cambridge, UK.

Golla et al., Analysis of cerebral responses to flicker in patients complaining of episodic headache, EEG Clin. Neurophys. 1959, pp. 539-549, vol. 11, No. 3, Burden Neurological Institute, Bristol, England.

Gordon et al., Algebraic Reconstruction Techniques (ART) for Three-dimensional Electron Microscopy and X-ray Photography, J. theor. Biol. 1970, pp. 471-481, vol. 29, No. 3, State University of New York at Buffalo, Amherst, NY.

Lempka et al., Theoretical Analysis of the Local Field Potential in Deep Brain Stimulation Applications, PLOS One 2013, e59839, vol. 8, No. 3, Department of Biomedical Engineering, Cleveland Clinic Foundation, Cleveland OH.

Liu et al., A description for computed tomography based on sinusoidal curves, Journal of X-Ray Science and Technology 2003, pp. 205-218, vol. 11, No. 4, University of Oxford, John Radcliffe Hospital, Oxford, UK.

Pollo et al., Directional deep brain stimulation: an intraoperative double-blind pilot study, Brain 2014, pp. 2015-2026, vol. 137, No. 7, Oxford University Press on behalf of the Guarantors of Brain.

Preibisch et al., Efficient Bayesian-based Multi-View Deconvolution, Nat. Methods 2014, pp. 645-648, vol. 11, No. 6.

Webb et al., Three-dimensional display of data obtained by single photon emission computed tomography, 1987, pp. 557-562, vol. 60, No. 714, Institute of Cancer Research and Royal Marsden Hospital, Carshalton, Surrey, London.

Yanch et al., Deconvolution of emission tomographic data: a clinical evaluation, The British Journal of Radiology, 1988, pp. 221-225, vol. 61, No. 723, Institute of Cancer Research and Royal Marsden Hospital, Carshalton, Surrey, London.

* cited by examiner

METHOD AND SYSTEM FOR PHYSIOLOGICAL TARGET LOCALIZATION FROM MACROELECTRODE RECORDINGS AND MONITORING SPINAL CORD FUNCTION

CROSS-REFERENCE TO RELATED APPLICATIONS

This application claims the benefit of U.S. Provisional Patent Application No. 62/039,559, filed Aug. 20, 2014, the contents of which are incorporated herein by reference in their entirety.

FIELD OF THE INVENTION

This invention relates to methods and systems to physiologically identify the spatial location of neural structures, including but not limited to structures in the brain, targeted during the course of deep brain stimulation-lead surgical implantation utilizing macroelectrodes and evoked potentials to vibratory, cutaneous electrical and peripheral nerve stimulation and also for recording of electromyographic activity. In addition, the invention provides for recording and analyzing long latency transcortical reflexes for monitoring spinal cord function and integrity.

This invention further relates to computer programs for high resolution localization of the evoked potentials.

BACKGROUND OF THE INVENTION

The primary purpose of target localization is to identify within a three-dimensional space the region in which deep brain stimulation (DBS) will produce optimal benefit. Further, targets must be identified and avoided, lest stimulation produce adverse effects. The primary targets for efficacy in the globus pallidus interna (GPi) and the ventral intermediate nucleus of the thalamus (Vim) are the appropriate homuncular representation within sensorimotor regions. With respect to the subthalamic nucleus (STN), it is just the sensorimotor region. Primary targets to be avoided include the posterior limb of the internal capsule in both the GPi, STN, and Vim; the optic tract in GPi; and the medial lemniscus and oculomotor nerve roots in STN DBS. To date, microelectrode recordings (MERs) of extracellular action potentials are the only effective mechanism. However, MERs add significantly to cost and risk.

It can be possible to use local field potentials; however, the issue is whether the resolution of local field potentials within the sensorimotor homunculus is sufficient to allow precise localization within a specific region of the homunculus as is necessary for larger structures such as GPi and Vim as well as to identify structures whose stimulation is to be avoided. Current interest of using local field potentials (LFPs) to identify regions of high beta oscillations are problematic and in the end, not of sufficient reliability.

Somatosensory evoked potentials from stimulation of the median nerve have been measured (Dinner D S, Neme S, Nair D, Montgomery E B Jr, Baker K B, Rezai A, Lüders H O. *EEG and evoked potential recording from the subthalamic nucleus for deep brain stimulation of intractable epilepsy.* Clin Neurophysiol. 2002 September; 113(9):1391-402). As shown in that work, evoked potentials in the subthalamic nucleus are relatively later than the appearance of the evoked potential recorded over the scalp and representing a cortex, consequently, recordings from the medial lemniscus precede those in the subthalamic nucleus. That work also shows phase reversal centered at the middle contact on the DBS lead which is evidence of origin of the evoked potential from within the subthalamic nucleus.

The objective of the person using the invention is to rapidly and efficiently physiologically identify specific regions in the nervous system, including but not limited to the brain, in order to accurately place therapeutic devices or agents, including but not limited to the deep brain stimulation (DBS) lead or injection cannula for biologics. Recording of long latency transcortical reflexes allows rapid assessment of the spinal cord such as but not limited to spinal cord surgery.

SUMMARY OF THE INVENTION

The invention described herein uses evoked potentials in local field potential (LFP) recordings in response to peripheral sensory and neural stimulation to guide device or electrode placement/implantation during surgery. Suitable types of stimulation include cutaneous electrical stimulation and vibration over muscles. This is particularly important in Vim DBS where Vim must be distinguished for tactile or posterior ventral caudal thalamus (Vc-tactile). The system and method of the present invention accomplish this task. Muscle spindles can be selectively activated by pulse vibratory stimulation applied using mechanical transducers. Muscle spindle activation increases lower motor neuron excitability to increase the probability of detecting long latency transcortical reflexes.

To this end, provided herein is a method of stimulating the peripheral nervous system of the patient, including the steps of recording, using a recording electrode inserted within a region of interest in the patient, a field potential evoked from the stimulation; calculating, using at least one processor, an evoked potential from the stimulation; advancing the recording electrode along a trajectory; determining, using at least one processor, a position along the recording electrode at which the evoked potential is largest; determining, using at least one processor, a distance r from the point on the recording electrode where the evoked potential is largest to a source of the evoked potential; and determining, using at least one processor, whether r is less than a predetermined threshold, wherein the predetermined threshold Y, wherein the predetermined threshold Y is the radius of an effective volume of tissue activation with an intended therapeutic brain stimulation for an intended target of brain stimulation.

In some embodiments of the method, the distance r is calculated using a Radon transform or variation thereof. In other embodiments, the recording electrode is a segmented lead electrode, and the distance r is calculated using the equation $r=((V_0^2/V_x^2-1)^{1/2})/d_x$, wherein $V_0$ is the potential at an electrode recording the highest evoked potential, $V_x$ is the potential at any other electrode, and $d_x$ is the distance from the electrode having potential $V_0$ and the electrode having potential $V_x$.

Also provided herein is a system for implanting a medical device within a patient. The system includes a recording electrode, at least one stimulator, at least one processor in communication with the recording electrode and the at least one stimulator, and a non-transitory computer readable medium in communication with the at least one processor and having one or more computer programs stored thereon that when executed by the one or more processors cause the at least one processor to perform the operations of stimulating the peripheral nervous system of the patient, recording a field potential evoked from the stimulation, calculating, using at least one processor, an evoked potential from the stimulation, determining, using at least one processor, a distance r from the recording electrode to a source of the evoked potential, determining, using at least one processor, whether r is less than a predetermined threshold Y, and advancing the electrode if r is greater than Y.

In some embodiments of the system, the stimulation used on the peripheral nervous system is mechanical. In other embodiments, the stimulation is electrical. In further embodiments, the stimulation is both mechanical and visual.

In some embodiments of the method, the distance r is calculated using and algebraic deconvolution, a Radon transform or variation thereof. In other embodiments, the recording electrode is a segmented lead electrode, and the distance r is calculated using the equation $r=((V_0^2/V_x^2-1)^{1/2})/d_x$, wherein $V_0$ is the potential at an electrode recording the highest evoked potential, $V_x$ is the potential at any other electrode, and $d_x$ is the distance from the electrode having potential $V_0$ and the electrode having potential $V_x$.

Also provided herein is a method of planning a trajectory for an implantable medical device in the brain of a patient. The method includes the steps of inserting a recording electrode within a portion of the patient's brain, stimulating the patient's peripheral nervous system and the patient's visual system, recording evoked potential data within the patient's brain using the recording electrode, applying, using at least one processor, a deconvolution algorithm to the evoked potential data to determine a distance from the electrode to a source of the evoked potential, and determining, using at least one processor, whether the distance is greater than or less than a threshold, and advancing or stopping the electrode based on the results of the determination.

Also provided herein is a system for implanting a medical device within a patient. The system includes at least one processor adapted to be in communication with a recording electrode and at least one stimulator and a non-transitory computer readable medium in communication with the at least one processor and having one or more computer programs stored thereon that when executed by the one or more processors cause the at least one processor to perform the operations of recording a field potential evoked from stimulation of the patient's nervous system, calculating, using at least one processor, an evoked potential from the stimulation, determining, using at least one processor, a distance r from the recording electrode to a source of the evoked potential, and determining, using at least one processor, whether r is less than a predetermined threshold Y.

Also provided herein is a method of performing spinal surgery on a patient including the steps of stimulating a muscle of the patient; recording, using at least one electrode, an electromyographic response to the stimulation; calculating, using at least one processor, a long latency transcortical reflex based on the stimulation and the electromyographic response; and determining, based on the occurrence of a long latency transcortical reflex, whether the spinal cord is intact. In some embodiments, the stimulation is a mechanical stimulation. In some embodiments, the stimulation further includes stimulation of the patient's peripheral nervous system. In further embodiments, the stimulation of the patient's peripheral nervous system comprises stimulation of a nerve that supplies the muscle that is stimulated.

DETAILED DESCRIPTION OF THE INVENTION

Figure 1:
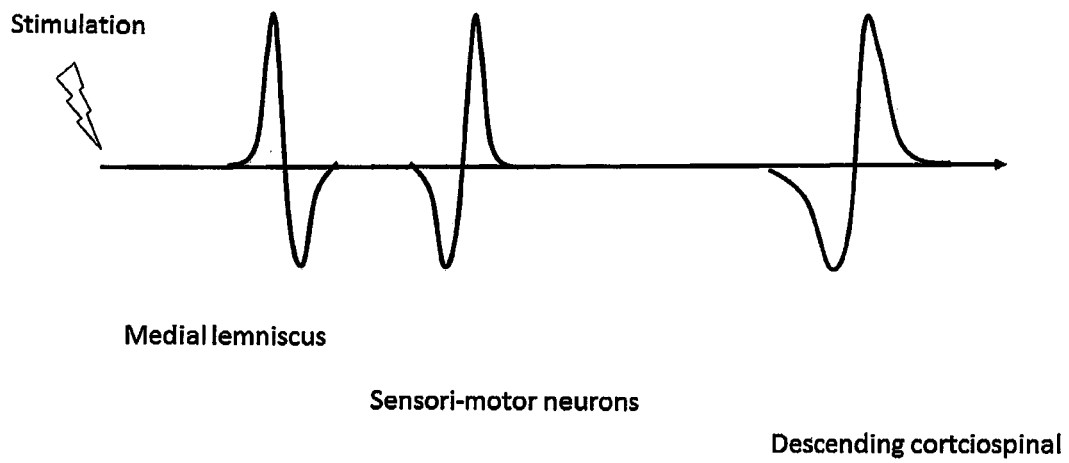
FIG. 1 shows a hypothetical time course of various evoked potentials recorded from a macroelectrode in a subthalamic nucleus. The time of stimulation is indicated by the figure of the lightning bolt. The evoked potential from the medial lemniscus occurs first as this pathway is made up of second order neurons that are one synapse removed from the stimuli. The second potential represents activation of sensorimotor neurons in the subthalamic nucleus that are at least third or fourth order neurons and consequently occur later. The last evoked potential is the volley in the descending corticospinal tract corresponding to the transcortical reflex that is at least 5 orders removed from the stimuli.

The present invention will now be described in detail by describing various illustrative, non-limiting embodiments thereof with reference to the accompanying drawings. The invention can, however, be embodied in many different forms and should not be construed as being limited to the illustrative embodiments set forth herein. Rather, the embodiments are provided so that this disclosure will be thorough and complete, and will fully convey the concept of the invention to those skilled in the art. The claims should be consulted to ascertain the true scope of the invention.

All references cited within this specification are incorporated by reference herein in their entirety.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention can assume various alternative variations and step sequences, except where expressly specified to the contrary. It is also to be understood that the specific devices and processes illustrated in the attached drawings, and described in the following specification, are simply exemplary embodiments of the invention. Hence, specific dimensions and other physical characteristics related to the embodiments disclosed herein are not to be considered as limiting.

The use of numerical values in the various ranges specified in this application, unless expressly indicated otherwise, are stated as approximations as though the minimum and maximum values within the stated ranges are both preceded by the word "about". In this manner, slight variations above and below the stated ranges can be used to achieve substantially the same results as values within the ranges. Also, unless indicated otherwise, the disclosure of these ranges is intended as a continuous range including every value between the minimum and maximum values. For definitions provided herein, those definitions refer to word forms, cognates, and grammatical variants of those words or phrases.

As used herein, the term "a" refers to one or more.

As used herein, the term "patient" refers to members of the animal kingdom including but not limited to mammals and human beings and is not limited to humans or animals in a doctor-patient or veterinarian-patient relationship. "A patient" refers to one or more patients such that a treatment effective in "a patient" refers to a treatment shown effective in one patient or a statistically significant number of patients in a population of patients.

As used herein, the terms "comprising," "comprise", or "comprised," and variations thereof, are open-ended and do not exclude the presence of other elements not identified. In contrast, the term "consisting of" and variations thereof is intended to be closed and excludes additional elements in anything but trace amounts.

As used herein, the terms "communication" and "communicate" refer to the receipt, transmission, or transfer of one or more signals, messages, commands, or other type of data. For one unit or device to be in communication with another unit or device means that the one unit or device is able to receive data from and/or transmit data to the other unit or device. A communication can use a direct or indirect connection, and can be wired and/or wireless in nature. Additionally, two units or devices can be in communication with each other even though the data transmitted can be modified, processed, routed, etc., between the first and second unit or device. For example, a first unit can be in communication with a second unit even though the first unit passively receives data and does not actively transmit data to the second unit. As another example, a first unit can be in communication with a second unit if an intermediary unit processes data from one unit and transmits processed data to the second unit. It will be appreciated that numerous other arrangements are possible. Any known electronic communication protocols and/or algorithms can be used such as, for example, TCP/IP (including HTTP and other protocols), WLAN (including 802.11 and other radio frequency-based protocols and methods), analog transmissions, Global System for Mobile Communications (GSM), and/or the like.

As used herein, the terms "electrode", "recording electrode", and "depth electrode" refer to electrodes that are suitable for placement within a body to measure electrical potentials, for example and without limitation local field potentials and evoked potentials. Such electrodes can be used in intracranial applications but are not limited to such purposes.

As used herein, the term "local field potential" (LFP) refers to the potential, or voltage, across the synapse of multiple neurons. The field potential can be measured by electrodes, recording electrodes, or depth electrodes, and can be measured during a quiescent or stimulated state. When the field potential is measured during a stimulated state, such field potential is referred to as an evoked potential.

As used herein, the term "evoked potential" refers to the detectable electrical activity representing a summation of electrical signals generated by cells, as in particular neurons. The evoked potential can be the result of the stimulation of a portion of the body, for example of an extremity such as an arm or leg, or portions thereof, whereby sensory neurons are excited and changes in electrical potential across a sensory pathway result. The evoked potential is detected by use of an electrode, recording electrode, or depth electrode.

As used herein, the term "stimulation" refers to any type of stimulation capable of causing propagation of a signal along the sensory pathway and evoking a local field potential, for example within the brain. Stimulation as used herein can refer to sensory stimulation of the tactile/somatic, visual, olfactory, nociceptive, auditory, and/or gustatory. Stimulation can be electrical stimulation through use of stimulatory electrodes, either transcutaneous or implanted/embedded, mechanical/vibrational stimulation through use of any suitable mechanical device, and sensory stimulation, for example visual through presentation of light or images, or olfactory through presentation of scents or smells.

While the following description describes the present invention in terms of localization of electrodes for deep brain stimulation (DBS), and thus implicitly describes cortical and subcortical structures as areas of evoked potential recording, those of skill will understand that the system and method described herein are not so limited and can be useful in any area where evoked potentials can be detected, for the precise and rapid placement of electrodes. The present system and method are also useful for placement of other medical devices than DBS electrodes, for example implanted stimulators, cannulae for providing biologics or pharmaceuticals, osmotic pumps, and any medical device in which the placement of the device is critical, and avoidance of critical structures (cortical, subcortical, or outside of the brain) is of utmost importance.

The invention described herein uses evoked potentials in LFP recordings in response to peripheral sensory and neural stimulation to guide medical devices or electrodes during surgery. Types of stimulation include cutaneous electrical stimulation and vibration over muscles. This is particularly important in Vim DBS where Vim must be distinguished for tactile or posterior ventral caudal thalamus (Vc-tactile). The stimulation just described can accomplish the task. Muscle spindles can be selectively activated by pulse vibratory stimulation applied using mechanical transducers. Muscle spindle activation increases lower motor neuron excitability to increase the probability of detecting long latency transcortical reflexes.

Figure 2:
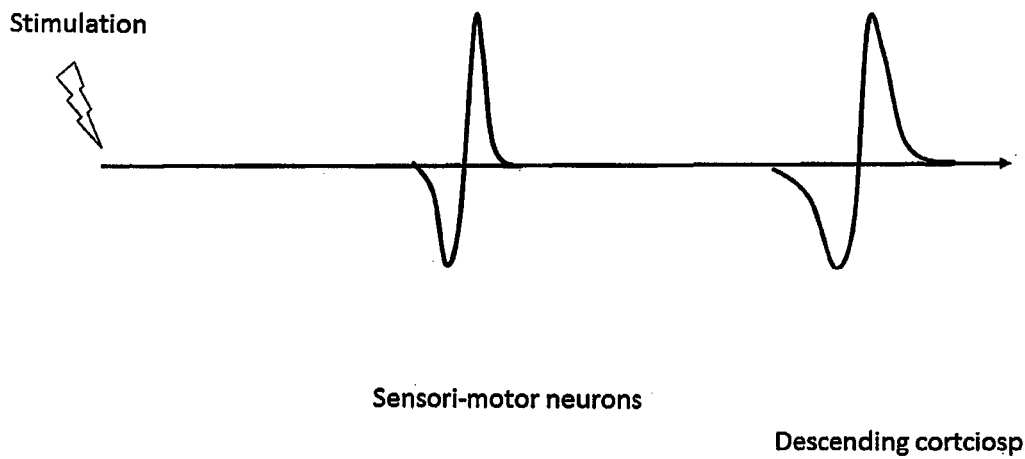
FIG. 2 shows a hypothetical time course of various evoked potentials recorded from a macroelectrode in globus pallidus interna
Figure 3:
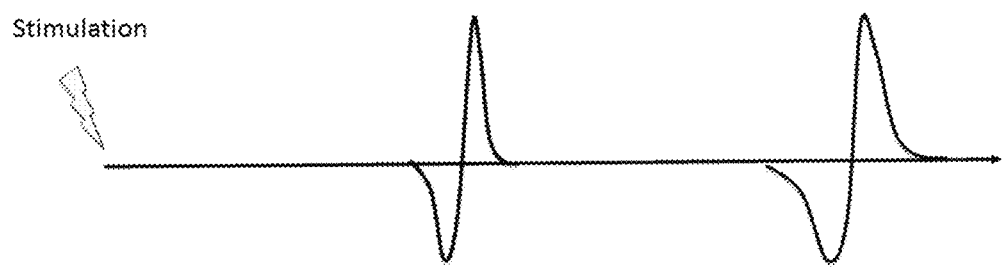
FIG. 3 shows a hypothetical time course of various evoked potentials recorded from a macroelectrode in the thalamus. The sensory evoked potentials are modality specific. An evoked potential associated with a burst of muscle vibration would be driven by muscle spindles and would be associated with the ventral intermediate thalamus. Electrical stimulation of the skin surface would be associated with activation of the posterior or tactile ventral caudal thalamus. The descending corticospinal tract activation would result from stimulation of a peripheral nerve producing a transcortical (i.e. long latency) reflex.

A potential problem is that there can be multiple structures that convey sensory information in the vicinity of the desired target. For example, posterior to the STN lies the medical lemniscus. Thus, techniques are required to differentiate the evoked potential arising from the medial lemniscus from the sensorimotor region of the STN. One approach is to determine the timing of the evoked potential in response to peripheral sensory stimulation. FIGS. 1-3 demonstrate a hypothetical example of the evoked potentials and their relative timing.)

Figure 4:
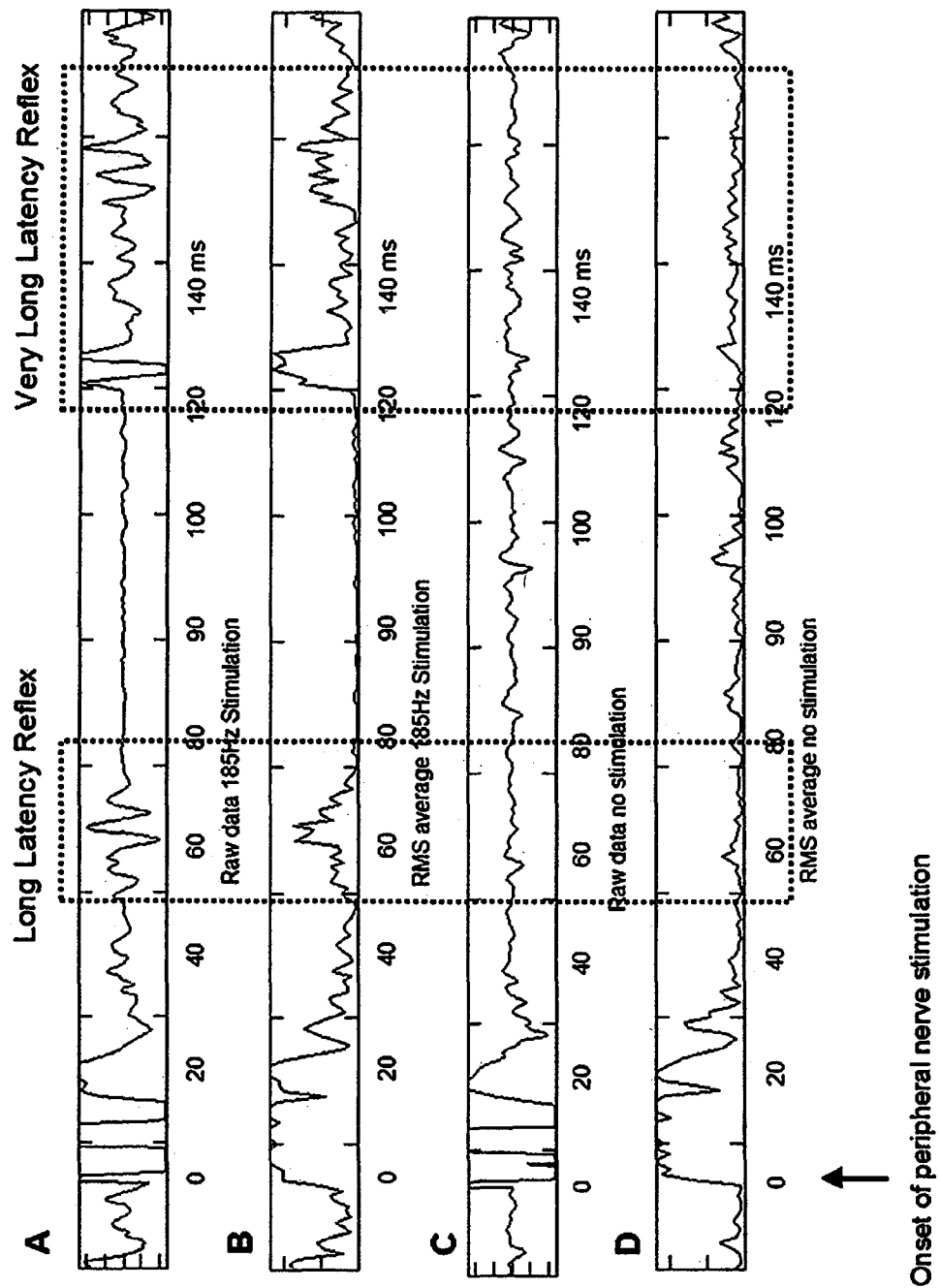
FIG. 4 shows results demonstrating the long latency reflex recorded from the flexor carpi ulnaris in response to stimulation of the ulnar nerve.

The evoked potential in the medial lemniscus is a result of the second-order neuron in the spinothalamic pathway and/or the second order neuron within the medial lemniscus pathway. The evoked potential in the STN would be at least a third or fourth order response and consequently follows the response in the medial lemniscus by 3-4 ms. Consequently, the evoked potentials recorded in the LFPs can be demarcated by those that are the first following the peripheral stimulation (referable to the medial lemnsicus) and those that follow at least 4 ms later which likely represent the sensory response within the STN. The same approach can be applied to peripheral stimulation with cutaneous nerve stimulation versus muscle vibration to differentiate the ventral caudal posterior nucleus of the thalamus from Vim. FIG. 4 demonstrates results from a study of transcortical (long latency) reflexes as proof of concept.

Specifically, subjects with Parkinson's disease who had successful STN DBS participated in the proof-of-concept study. The subjects withheld their usual first morning dose of anti-parkinson medications for the experimental session. The subjects were seated comfortably with their forearms resting in a manipulandum that maintained the wrist in neutral position with the fingers extended. The surface electromyographic (EMG) electrodes likely pick up both finger and wrist flexors as they are in close proximity in the forearm, therefore ring finger and wrist flexor actions were utilized to remove potential confounds. Requiring the subjects to maintain their fingers extended during the flexion force caused the finger flexor muscles to be engaged with the wrist flexors in producing the wrist flexion force.

Muscles participating in generating a flexion force around the wrist were identified by palpation. Two sets of pairs of surface EMG electrodes (each 5 mm in diameter) separated by approximately 10 mm were placed over the flexor carpi ulnaris muscles contralateral to the hemisphere being stimulated following removal of surface oils and mild abrasion of the skin. EMG signals were amplified in bipolar mode with the indifferent electrode over the olecranon. Two EMG signals were recorded from each subject. Typical gains were 10 k, high pass filtered at 100 Hz, low pass filtered at 100 kHz, with the 60 Hz notch filter engaged (Model 15 Neurodata System with high bandwidth amplifiers, Grass Instruments Inc.). The analogue data was analogue-to-digital converted at 12 k-samples per second.

Bipolar stimulating electrodes were placed over the ulnar nerve posterior to the medial epicondyle. Charge balanced biphasic constant current square wave pulses were delivered singly with each phase duration at 4 ms. The current was increased to the first visible contraction of the flexor carpi ulnaris, typically 5-7 milliamps. This suprathreshold current was used in the experiments.

Subjects were asked to make a maximum voluntary flexion force with visual feedback of the forces generated. Once the maximum force plateaued, a single stimulation pulse was applied to the ulnar nerve. As the wrist and finger flexors were fixed in the manipulandum the resulting muscle contraction was isometric thereby minimizing movement of the muscles beneath the surface electrodes thus ensuring relative stability of the EMG recordings.

DBS parameters, such as voltage, pulse width and configuration of active electrode contact, found effective in prior routine clinical care were used during the experiments with the exception of frequency. The following DBS frequencies were used, high frequency stimulation found to be therapeutically effective during prior routine clinical care and 70, 20 and 0 pps.

Considerable inter-subject variability in the optimal DBS configurations and parameters was anticipated. As the purpose of the research is to investigate the mechanisms underlying clinical efficacy, the experimental conditions should reflect clinically optimal settings. Attempting to use the same electrode configurations and stimulation parameters across all subjects risks sub-optimal stimulation for some subjects and thus, confound the investigation to determine therapeutic mechanisms. Consequently, selection of electrode configurations and stimulation parameters were based on those settings found optimal during routine clinical management prior to participation in the research.

Eleven stimulations were performed for each DBS condition. The EMG signals were Root Mean Square (RMS) converted (FIG. 4). The RMS EMG was averaged over the 11 trials (data not shown). The peak in the RMS EMG in the time interval of 50-100 ms, which is the latencies typically associated with Long Latency Reflexes, were determined. The difference between the peaks and the average RMS EMG just prior to the ulnar nerve stimulation were calculated. An Analysis of Variance with repeated measures design (ANOVAr) and Tukey post-hoc comparisons were used for statistical analysis.

The subjects were not informed of the DBS conditions. However, in an effort to assure the most critical conditions were tested during each session, DBS conditions were conducted in the following order; therapeutic high frequency, 0, 20, and then 70 pps DBS. DBS at 20 pps was selected because of hypotheses that there is an abnormal increased power in the 20 Hz range in the basal ganglia-thalamic-cortical system and that 20 pps DBS worsens parkinsonian symptoms whereas high frequency DBS improves symptoms.

Subjects were tested only after 10 minutes following the change in DBS conditions. The order of DBS conditions provided the most conservative test of the main hypothesis, which was that high frequency DBS would increase the magnitude of the long latency reflexes compared to the no DBS condition. Any carryover or practice effects from the initial high frequency DBS condition would be expected to increase the magnitude of the long latency reflexes during the no DBS condition. Thus, demonstration of a statistically significant increase during high frequency DBS over no DBS would be robust.

During the course of the experiments, another longer latency reflex was found with a latency between 100 to 200 ms following the ulnar nerve stimulation (FIG. 4). This is termed the Very Long Latency Reflex. Statistical analyses of the difference between peaks in this time interval to the pre-stimulation RMS EMG were conducted as described above.

Seven subjects underwent testing. Subject characteristics and optimal DBS parameters and configurations are shown in the table. An example of the raw and RMS EMG recordings for one subject is shown in FIG. 4. As can be seen, under the high frequency DBS, there is a robust increase in the RMS EMG approximately 50-80 ms following the peripheral nerve stimulation consistent with the Long Latency Reflex. Also, another EMG response is seen approximately 120 ms following the peripheral nerve stimulation or the Very Long Latency Reflex.

Figure 5:
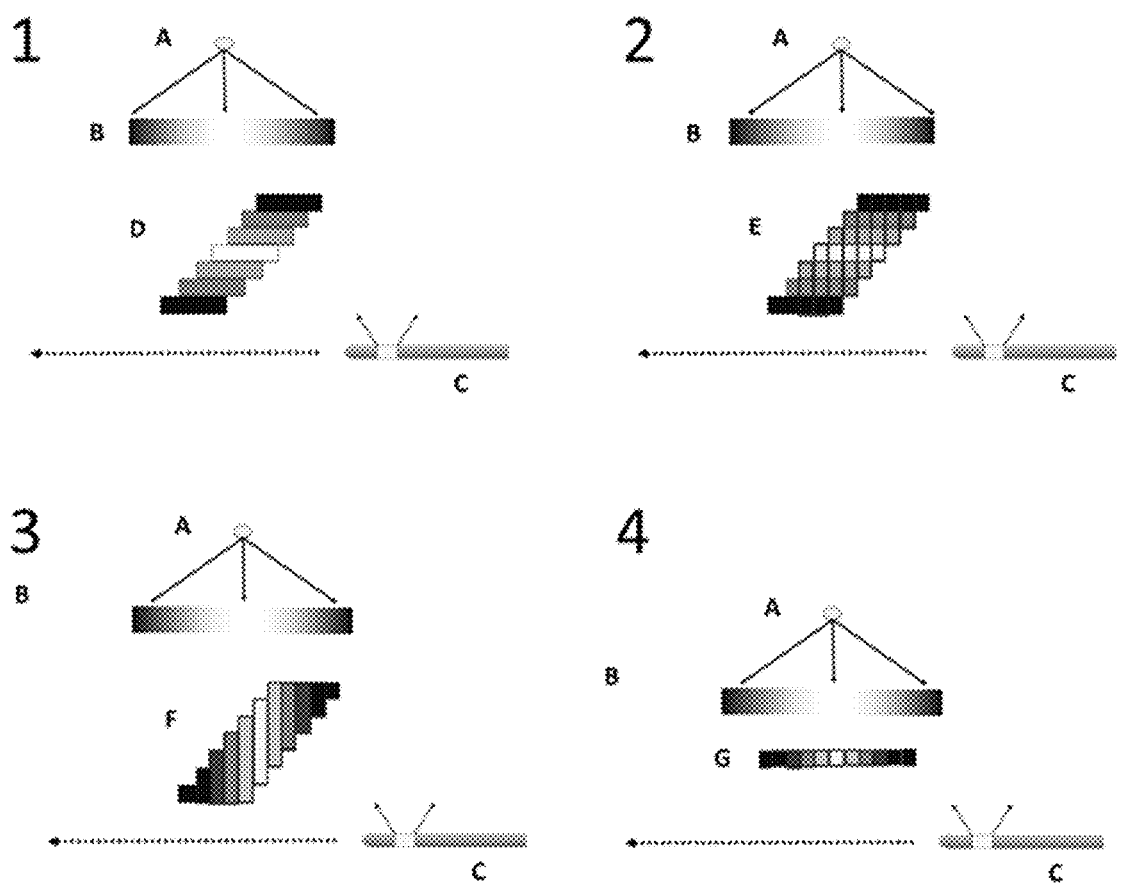
FIG. 5 shows a schematic representation of one non-limiting approach for source localization according to the present invention. In each numbered panel, the source of the evoked potential is shown by (A). Any point is space will see the evoked potential voltage reduced by its distance from the source (B). As an electrode (C) is moved from left to right in small incremental steps (much smaller than the length of the electrode), the voltage recorded will change. However, the voltage recorded represents the integral of the voltages over the length of the electrode thereby burring the signal and reducing resolution of the source localization (D). As seen in C, the segment of the electrode within a single column, represented by the vertical red rectangle, has the same potential in the evoked potential which is different from adjacent columns (F). As the overlapping segments of each recorded evoked potentials recorded at each position of the electrode are set to the same potential, the potentials assigned to the non-overlapping segments are adjusted. However, this adjustment is constrained by the other overlapping segments from other positions of the electrode. As can be seen in (G), the resolution of the re-constructed potentials is proportional to the extent of the overlap. Further, the intensities of the resolved segment relates to the distance from the evoked potential signal source. Also, the change in the maximum potential as the electrode is moved indicates whether the contact is moving towards or away from the source.

The above results show that long latency reflexes can be discerned. However, in order to identify the homuncular representation, sensory stimulation is applied to the skin surface in the proximal and distal upper and lower extremities and to the face (FIG. 5). Muscle vibration using a mechanical stimulator (3, 4) is applied over muscles in the proximal and distal upper and lower extremities and over the masseter muscle in the head.

A similar approach can be used for identifying the location of the optic tract for GPi DBS lead implantation surgery. The corticospinal tract activation can utilize transcortical motor evoked potentials (also known as long latency reflexes) in response to electrical stimulation of the peripheral nerve(s) using an electrical stimulator (2). Such stimulation first produces an M-wave (from orthodromic activation of motor nerve fibers), an F-wave (from antidromic activation of lower motor neurons), an H-reflex (from antidromic activation of sensory nerve fibers that reflexively activate lower motor neurons), and then the transcortical reflex (from ascending activations to the somatosensory cortex, to the motor cortex, descending the corticospinal tract, and finally activating the lower motor neuron to produce a motor unit response). It is the descending volley of action potentials that can be identified in the LFP to indicate the location of the corticospinal tract. Again, the timing of the evoked potential identifies the potential generated in the corticospinal tract. To evoke the long latency transcortical reflex evoked potential, suprathreshold stimulation would be applied to peripheral nerves, including but not limited to the median and posterior tibialis nerves.

An aspect of the invention described here is to use evoked potentials in the LFP recordings in response to peripheral sensory stimulation. Types of stimulation include cutaneous and peripheral nerve electrical stimulation, flashing lights (photic) over the eyes, and vibration over muscles or rapid short amplitude rotations about the joint through which the muscle acts. This is particularly important in Vim DBS where Vim must be distinguished for tactile or posterior ventral caudal thalamus (Vc-tactile). Muscle spindles can be selectively activated by pulse vibratory stimulation applied using mechanical transducers.

Current source localization methods rely on high density three-dimensional arrays with fine spacing and small electrical contacts. Methods used in this context include relative differences in amplitudes among electrodes in the array and phase reversal between specific electrodes in the array. However, such arrays would be highly problematic in DBS surgery. Further, there is a fundamental limit on the ability to localize the source that limits spatial resolution on the order of several millimeters using these methods (Lempka S F, McIntyre C C. *Theoretical analysis of the local field potential in deep brain stimulation applications*. PLoS One. 2013; 8(3):e59839). Thus, it is unlikely that LFPs as currently used will have sufficient spatial resolution for the precision required in the delivery of medical devices and electrodes during surgical procedures involving the nervous system, particularly the central nervous system.

The invention includes systems and methods for localization of electrophysiological signals using the movement of a single or set (whether in pairs or otherwise more than one) of electrodes through the brain while simultaneously recording evoked potential from peripheral stimulation as described above (FIG. 5). The concept is that a single electrode (or the difference between a pair of electrodes in bipolar configuration) shows multiple views of the same signal source as it is advanced through the brain. The spatial localization is now determined not by the size of the electrical contact but by the size of the steps by which the electrode is moved, which can be on the order of microns if necessary.

More generally, one can conceptualize the single macroelectrode contact as a series of infinitely small electrical contacts and the field potentials as the sum or average of the signals in each infinitely small contact within the macroelectrode. Thus, within a single electrode macroelectrode, the information from the signal source is convoluted across all the infinitely small electrode signals. This concept can be applied to the entire trajectory through which the electrical contact moves (FIG. 5) and thus, the signals recorded throughout the trajectory are convolutions of the original single electrical source. Each signal is slightly different based on its distance to the signal source and the resistivity of the intervening conductor, such as the brain.

The invention can employ a number of deconvolution or reconstruction algorithms to extract the original signal which then greatly increases the spatial resolution and can be used to identify a point in three-dimensional space corresponding to the signal source. Many of these are based on Radon transformations (Liu J J, Watt-Smith S R, Smith S M. *A description for computed tomography based on sinusoidal curves*. J Xray Sci Technol. 2003 Jan. 1; 11(4): 205-18. While the Radon transform is typically utilized in image reconstruction in medical imaging, for example in computerized tomography (CT) scans, its principles can be applied to the present invention for determination of intensity (image in the case of CT or voltage as utilized herein) along a straight line.

Figure 15:
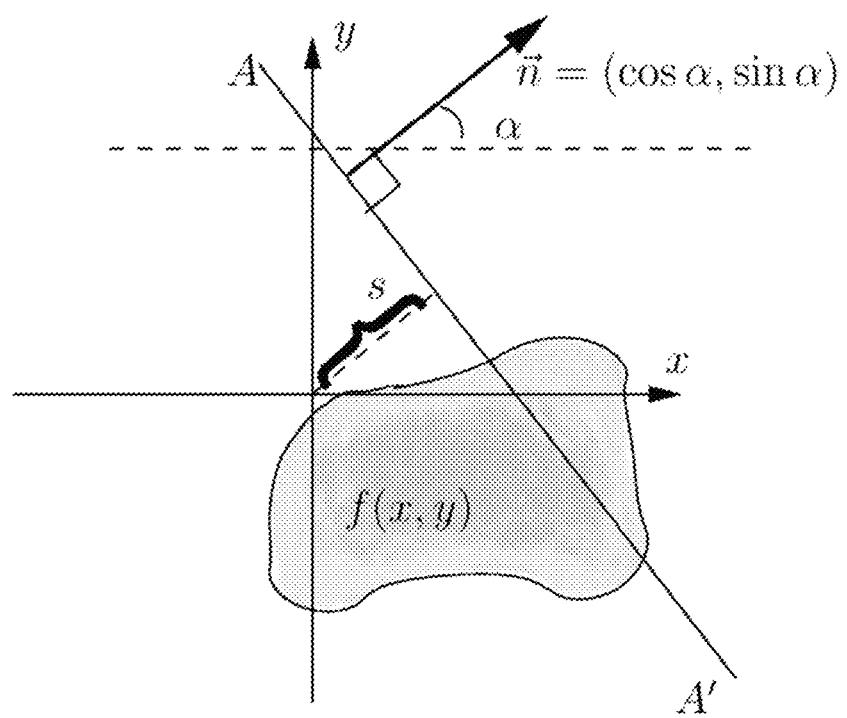
FIG. 15 shows an example of a Radon transformation.

With regard to the Radon Transformation, FIG. 15 shows the concept.

If $f(x)=f(x,y)$ is a compactly supported continuous function on $R^2$, the Radon transform, $Rf$, is a function defined on the space of straight lines L in $R^2$ by the line integral along each such line:

$$Rf(L)=\int_L f(x)|dx|.$$

The parametrization of any straight line L with respect to arc length t can be depicted as:

$$(x(t),y(t))=((t\sin\alpha+s\cos\alpha),(-t\cos\alpha+s\sin\alpha))$$

where:
s=the distance of L from the origin; and
α=the angle the normal vector to L makes with the x axis.

The quantities (α,s) can be considered as coordinates on the space of all lines in $R^2$, and the Radon transform can be expressed in these coordinates by the equation:

$$Rf(\alpha, s) = \int_{-\infty}^{\infty} f(x(t), y(t))dt$$
$$= \int_{-\infty}^{+\infty} f((t\sin\alpha + s\cos\alpha), (-t\cos\alpha + s\sin\alpha))dt$$

In the n-dimensional Euclidean space $R^n$, the Radon transform of a compactly supported continuous function $f$ is a function $Rf$ on the space $\Sigma_n$ of all hyperplanes in $R^n$, defined by the equation:

$$Rf(\xi)=\int_\xi f(x)d\sigma(x)$$

for $\xi\in\Sigma_n$, where the integral is taken with respect to the natural hypersurface measure, dσ (generalizing the |dx| term from the 2-dimensional case). Any element of $\Sigma_n$ is characterized as the solution locus of an equation:

$$x\cdot\alpha=s$$

where $\alpha\in S^{n-1}$ is a unit vector and $s\in R$. Thus the n-dimensional Radon transform can be rewritten as a function on $S^{n-1}\times R$ using the equation:

$$Rf(\alpha,s)=\int_{x\cdot\alpha=s} f(x)d\sigma(x).$$

It is also possible to generalize the Radon transform still further by integrating instead over k-dimensional affine subspaces of $R^n$. The X-ray transform is the most widely used special case of this construction, and is obtained by integrating over straight lines. The Radon transform can be utilized in a variety of programming languages/software environments, such as MATLAB (MathWorks, Natick, Mass. USA) and the open-source R software.

An example of a technique making use of the Radon transform and deconvolution is Computerized Tomography such as used in Single Photon Emission Tomography (SPECT) scans where the signal source (in this case the photon in space where a photon is released from a radioactive nuclei) is reconstructed from a series of detectors (Fokas A S, Iserles A and V. Marinakis V. *Reconstruction algorithm for single photon emission computed tomography and its numerical implementation*. J. R. Soc. Interface (2006) 3, 45-54; Yanch J C, Irvine A T, Webb S, Flower M A. *Deconvolution of emission tomographic data: a clinical evaluation*. Br J Radiol. 1988 March; 61(723):221-5; Floyd C E Jr, Jaszczak R J, Greer K L, Coleman R E. *Deconvolution of Compton scatter in SPECT*. J Nucl Med. 1985 April; 26(4):403-8; Webb S, Ott R J, Flower M A, McCready V R, Meller S. *Three-dimensional display of data obtained by single photon emission computed tomography*. Br J Radiol. 1987 June; 60(714):557-62). The source of the single photon in a SPECT scan can be analogized to the source of the electrophysiological evoked potential in the present invention, and the series of detectors used in SPECT would correspond to the series of field potentials recorded by the single or bipolar electrode as it moved through the brain. Another example is modern light-sheet microscopy (Preibisch S, Amat F, Stamataki E, Sarov M, Singer R H, Myers E, Tomancak P. *Efficient Bayesian-based multiview deconvolution*. Nat Methods. 2014 June; 11(6):645-8).

An alternative approach is to consider the average potential over the length of the electrical contact as oriented tangentially to the source. The length of electrical potential can then be rotated (FIG. 6) to point to a hypothetical source. The angle of rotation is adjusted to move the source on a line perpendicular and/or parallel to the orientation of the electrode trajectory until a specific movement of the hypothetical source results in the best fit to recorded potential. Deconvolution algorithms typically employed in X-ray CT scans can be used. Another and preferred algorithm is the Algebraic Reconstruction Technique, also utilized in processing/analysis of CT scan data (see Gordon R et al. *Algebraic reconstruction techniques (ART) for three-dimensional electron microscopy and x-ray photography*. J Theor Biol 1970 December; 29(3):471-481).

The present invention can accommodate recent advances in segmented DBS electrode leads to greatly increase the spatial localization of signal sources thereby greatly increasing the accuracy and efficiency of target localization (Pollo C, Kaelin-Lang A, Oertel M F, Stieglitz L, Taub E, Fuhr P, Lozano A M, Raabe A, Schüpbach M. *Directional deep brain stimulation: an intraoperative double-blind pilot study*. Brain. 2014 July (137):2015-2026.

In view of the above, the present invention includes a system and method to elicit evoked potentials from local field potentials resulting from the specific stimulation of peripheral neural structures. As shown schematically in FIG. 7, these include a combined system including surface electrodes (5) for stimulation of superficial nerves and to record electromyographic activity from the muscles below the mechanical stimulators (3, 4); a set of peripheral nerve stimulating electrodes; and a photic stimulator (8). Also, the recording electrode (1), in this example inserted into the brain, is connected to an amplifier/recording system to record local field potentials.

These stimulations evoke potentials within the brain that are detected by the recording electrode (1), which communicates with the computer system (7). For example, a photic stimulator provides flashes of lights that excite the optic tract which facilitates obtaining a photic evoked potential which would be generated in the optic tract.

Figure 7:
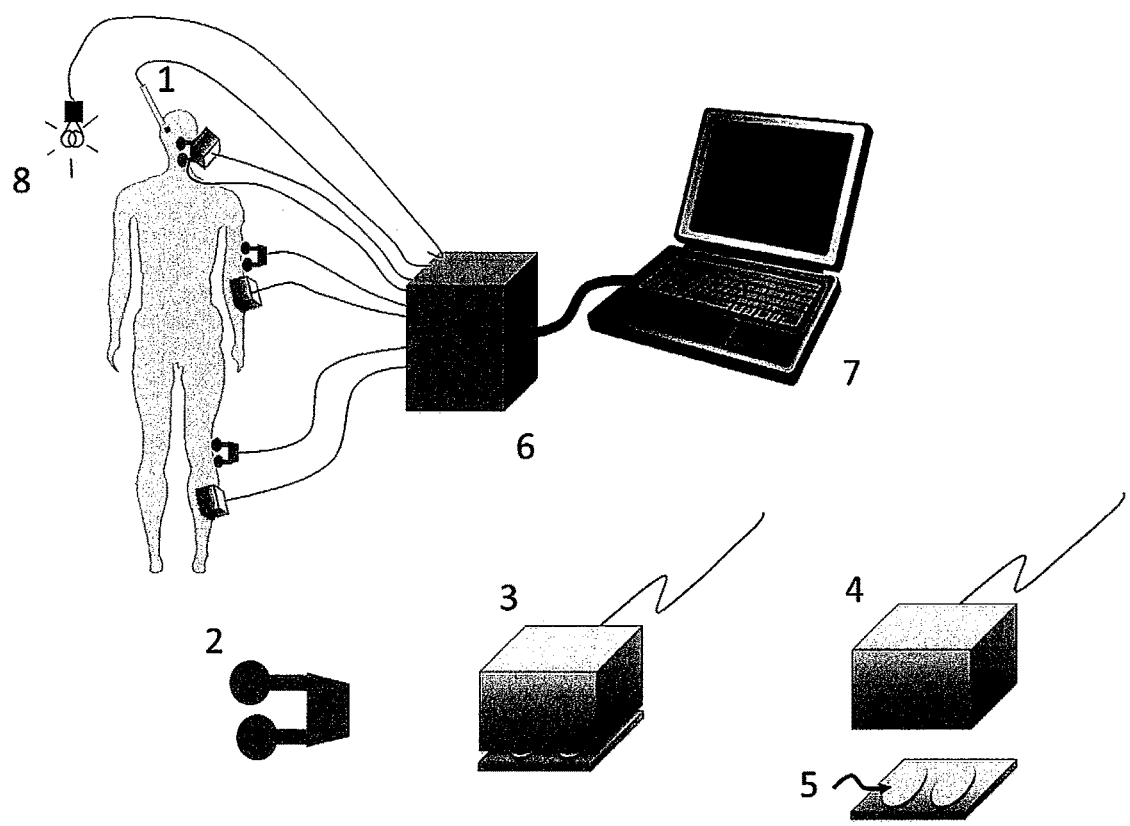
FIG. 7 shows a schematic representation of one non-limiting embodiment of a system according to the present invention.

As described above, this communication can be wired (i.e., the recording electrode (1) can be hard wired or directly connected to the computer (7)), or the communication between the recording electrode (1) and the computer (7) can be wireless, for example by WLAN or other wireless protocols and methods, by Bluetooth, ZigBee, EnOcean, TransferJet, Wireless USB, and the like known to those of skill in the art. Those of skill in the art will appreciate that wireless communication between devices is possible for transmission of recorded data from electrode (1) to computer system (7) and, in some embodiments, of instructions from computer system (7) to electrode (1). During the use of the invention during surgery, a recording electrode (1), as might be used in the brain, is in place to record the local field potentials in response to some combination of the stimulation described above and over the head, arm, and leg as represented in FIG. 7. A series of stimuli is presented and the local field potentials simultaneously recorded just before, during, and just after each stimulation. The epochs of local field potentials are visually inspected to reject epochs containing artifacts and then averaged to provide the evoked potentials (FIGS. 1-3).

Figure 6:
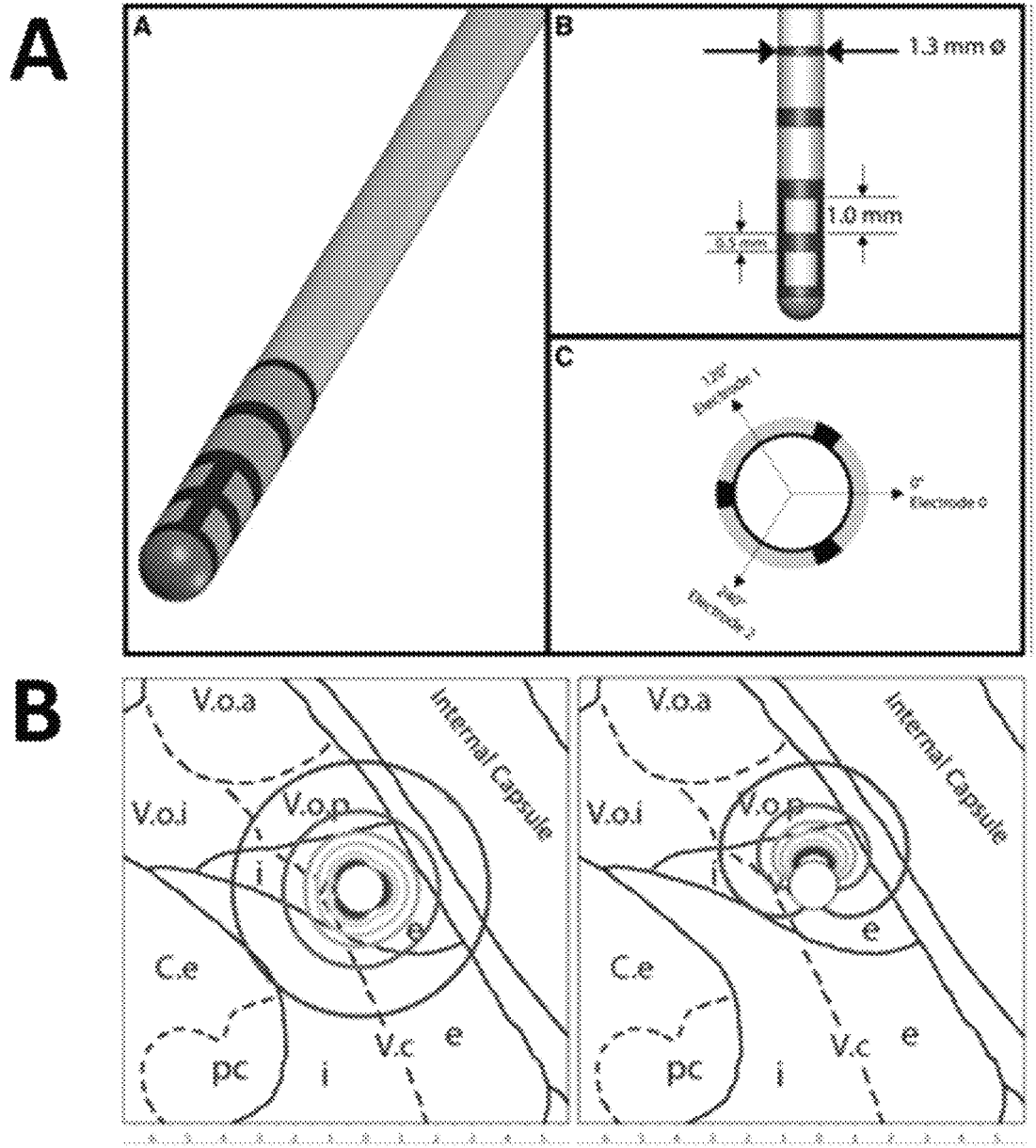
FIG. 6 shows a schematic of a segmented lead (A). A hypothetical description of the fields of electrical current distribution are shown in (B).

Recording electrodes (1) useful in the present invention can be any type known to those of skill in the art, available from a wide variety of commercial sources. For example, and without limitation, such electrodes are produced by Medtronic, Inc. (Minneapolis, Minn. USA), Boston Scientific Corp. (Valencia, Calif. USA), Sapiens Steering Brain Stimulation BV High Tech (AE EINDHOVEN, The Netherlands), St. Jude Medical, Inc. (St. Paul, Minn. USA), Ad-Tech Medical Instrument Corporation (Racine, Wiss. USA), and Integra (Plainsboro, N.J. USA). In one embodiment, the electrode is a segmented electrode, meaning that the electrode comprises more than one electrode for detection of field/evoked potential. An example of a segmented electrode is shown in FIG. 6. The electrodes can be disposed circumferentially or substantially circumferentially axially along the length of the electrode body. A segmented electrode useful in the present invention can include 2 or more electrodes, including 3, 4, 5, 6, 7, 8, 9, 10, or more electrodes. Those of skill in the art will appreciate that the present system and method are useful for any type of recording electrodes.

With continuing reference to FIG. 1, electrodes (1) suitable for recording evoked potentials in the present invention are advanced through tissue by suitable drives, such as microdrives available from commercial manufacturers. For example, and without limitation, electrodes (1) can be advanced using microdrives offered by FHC Inc. (Bowdoin, Me. USA) and AlphaOmega Co. USA, Inc. (Alpharetta, Ga. USA). Those of skill will understand that electrodes (1) and drives can communicate with interface (6) and/or computer system (7) by wired or wireless systems, as described herein. Any drive that allows for incremental advancement of a recording electrode will be suitable for use in the system and method of the present invention.

In some embodiments, the interface (6), which can provide communication between electrode (1) and computer system (7), and between mechanical stimulator(s) (3, 4) and stimulating electrodes (2) (which can be skin surface contact electrodes or implantable electrodes, depending on application and needs of the surgeon) and the computer system (7), includes an amplifier for amplifying the signal detected by electrode (1). Amplifiers are known to those of skill in the art, and are obtainable from numerous commercial sources, for example from Grass Technologies (Warwick, R.I. USA), FHC, Inc. (Bowdoin, Me. USA), AlphaOmega Co. USA, Inc. (Alpharetta, Ga. USA), and Medtronic, Inc. (Minneapolis, Minn. USA). In other non-limiting embodiments, the interface (6) includes one or more filters known to those of skill in the art for filtering electrical signals of field and evoked potentials. As is understood by those of skill in the art, filters are often included in the amplifier, such as those identified herein. Filters useful in the present system and method can be, for example and without limitation, band-pass filters. The blocking setting of the band-pass filter can be set to any useful threshold or range suitable for maximizing clarity of received data from electrode (1). While a typical filter setting can be in the range of 500 Hz (high pass) and 24 k Hz (low pass), those of skill in the art will appreciate and understand that those settings can be adjusted to provide the clearest signal possible.

With continuing reference to FIG. 7, in a method of the present invention, an evoked potential associated with the transcortical (long latency) reflex is recorded. Any suitable stimulation that causes a field potential that can be recorded by electrode (1) falls within the scope of the present invention and can be utilized for the evoked potential utilized by the computer system (7) to localize the electrode and aid in placement of electrodes for DBS. In one embodiment, the mechanical stimulation is by a vibrator (4) or other mechanical device providing tactile/somatic stimulation to a portion of the body. Examples of stimulation and relevant cortical and subcortical structures are shown in Table 1.

TABLE 1

| Stimulation type | Modality | Relevant DBS target | Relevant structure |
| --- | --- | --- | --- |
| Cutaneous (skin) electrical stimulation | Superficial sensation | Vim | Vc |
| Vibration | Deep sensation-muscle spindle, muscle specific | Vim | Vim, homuncular representation |
| | | Vim | Medial lemniscus |
| | | STN | Sensorimotor region |
| | | GPi | Sensorimotor region, homuncular representation |
| Peripheral nerve | Transcortical reflex-corticospinal tract | Vim, STN, GPi | Corticospinal tract |
| Photic | Visual system | GPi | Optic tract |

Devices for providing mechanical stimulation are known to those of skill in the art, and are widely available from commercial sources. In non-limiting embodiments, the vibrator/mechanical device is used to stimulate an extremity, such as a portion of the arm or leg of a patient. Stimulation can be of any duration and strength suitable to evoke a field potential within the region of interest for the surgeon. In non-limiting embodiments, the stimulation occurs for tens of milliseconds to tens of seconds with a 1-5 mm amplitude, and frequencies from 20 Hz to 220 Hz.

In other non-limiting embodiments, the evoked potential is the result of another type of stimulation, or one or more types of stimulation, such as tactile/somatic as described above, olfactory, gustatory, auditory, and/or visual. In a particularly preferred embodiment, stimulation is by tactile/somatic stimulation and by visual stimulation.

Olfactory and gustatory stimulation can be implemented with any smell/scent or taste useful for evoking a field potential known to those of skill in the art. Auditory stimulation can be implemented with any sound-emitting device known to those of skill in the art to be useful for evoking field potentials. For example, and without limitation, tuning forks, musical instruments, electronic tone generators, and the like are suitable for evoking potentials in the auditory cortex.

With further reference to sensory stimulation, as will be apparent to those of skill in the art, visual stimulation and detection of evoked potentials therefrom will be of importance so as to avoid critical optical tracts and regions of cortex and subcortical structures. Visual stimulation can be by presentation of photic stimulation, flashes of light, changes in color of presented light, dichoptic stimulation, prismatic stimulation, tachistoscopic stimulation, and the like. Those of skill in the art will appreciate that visual stimulation can take any form useful for evoking field potentials.

In non-limiting embodiments, the evoked potential is the result of peripheral nerve stimulation, a volley of electrical excitation ascends through the brain to the sensory cortex, then across to the motor cortex and subsequently, down the corticospinal tract to cause a long latency muscle contraction that can be recorded by the electromyographic (EMG) electrodes (5). The local field potentials associated with the volley of excitation descending the corticospinal tract are windowed in the appropriate latency and then averaged to produce an evoked response. The local field potentials are recorded as the macroelectrode advances in small incremental steps. Thus, at each position of the macroelectrode evoked potentials are recorded for each type of stimulation used over the head, arm, and leg. The local field potentials are windowed in time to ensure collection of electrical signals appropriate to the structures being identified.

In non-limiting embodiments, stimulation of the peripheral nerve for the transcortical reflex includes biphasic charge balance pulses, where each phase is 1 ms in duration. Single pulses can be applied, at an amplitude ranging from 1-10 times the threshold necessary to evoke a long latency EMG response. Those of skill in the art will appreciate that the strength of the pulse (in amplitude as a function of threshold) can be varied based on location and conditions. In a particular embodiment, the stimulation is 1.5 times the threshold necessary to evoke a long latency EMG response. Note, the thresholds can be established while the patient is under anesthesia during surgery and therefore, would not be uncomfortable for the patient. The peripheral nerves to be stimulated include the median nerve in the upper extremity and the posterior tibialis in the lower extremity. Note that the transcortical reflex need not be used for identification of the homuncular representation, but can be used only to elicit a volley of activity in the corticospinal tract; hence, precise reference to a specific peripheral nerve is not needed in the present method. The peripheral nerves selected are based on past experience with transcortical reflexes that will be familiar to those of skill in the art.

Cutaneous stimulation can consist of 10 pulses delivered at 300 pulses per second (pps) following the methods of Floeter et al. (Floeter M K, Gerloff C, Kouri J, Hallett M. *Cutaneous withdrawal reflexes of the upper extremity. Muscle Nerve.* 1998 Can; 21(5):591-8). Stimulation can be delivered as constant current at from 1 ms-1 second duration, in some embodiments 1 ms duration, using charge balanced biphasic pulses whose intensity is 1-10, in some embodiments 1.5, times the threshold to induce a cutaneous withdrawal reflex EMG response. Muscle spindle activation can be driven by a vibration of a rate of 20 to 200 Hz for 1 s. As those of skill will understand, the amplitude and frequency can be adjusted to determine the threshold to a long latency EMG response and during testing an amplitude and frequency 1.5 times the threshold was used.

Photic stimulation can utilize an electronic stroboscope, giving flashes of blue-white xenon light with a time constant of 1-100 μs, in some embodiments 15 μsec, frequency from 3.5 to 25 flashes per second (f/sec) without change in duration or brilliance and to 100 f/sec, at a reduced intensity. The peak intensity of the flash would be about 88,000 candles following the methods of Golla and Winter (Golla F L, Winter A L. *Analysis of cerebral responses to flicker in patients complaining of episodic headache.* Electroencephalogr Clin Neurophysiol. 1959 August; 11(3):539-49). The stroboscope can be placed from 1-100 cm, in an embodiment 10 cm, in front of the subject's nose. Local field potentials are recorded by an occipital electroencephalography (EEG) electrode at O1 (based on the International 10-20 convention for EEG electrode placement) for left-sided surgery or O2 for right-sided surgery. The occipital electrodes can be referenced to linked mastoid electrodes. Evoked potentials can be extracted from multiple epochs of local field potentials following each photic stimulus. Thus, the demonstration of a photic stimulus-associated evoked potential is demonstration of adequate photic stimulation.

The evolution of the evoked potentials with accumulating stimuli can be monitored in real-time. In cases of electrical stimulation, at the first appearance of an evoked potential, the polarities of the electrical stimulating electrodes can be reversed and an additional set of stimuli, equal in number to the stimuli delivered prior to reversal, are applied in order to cancel or reduce stimulus artifact. This method can be used to monitor the evolution of the evoked potential from the intra-cerebral macro-electrodes as well as the EMG evoked responses (note, the EMG responses will be RMS converted before averaging into an evoked response).

Figure 8:
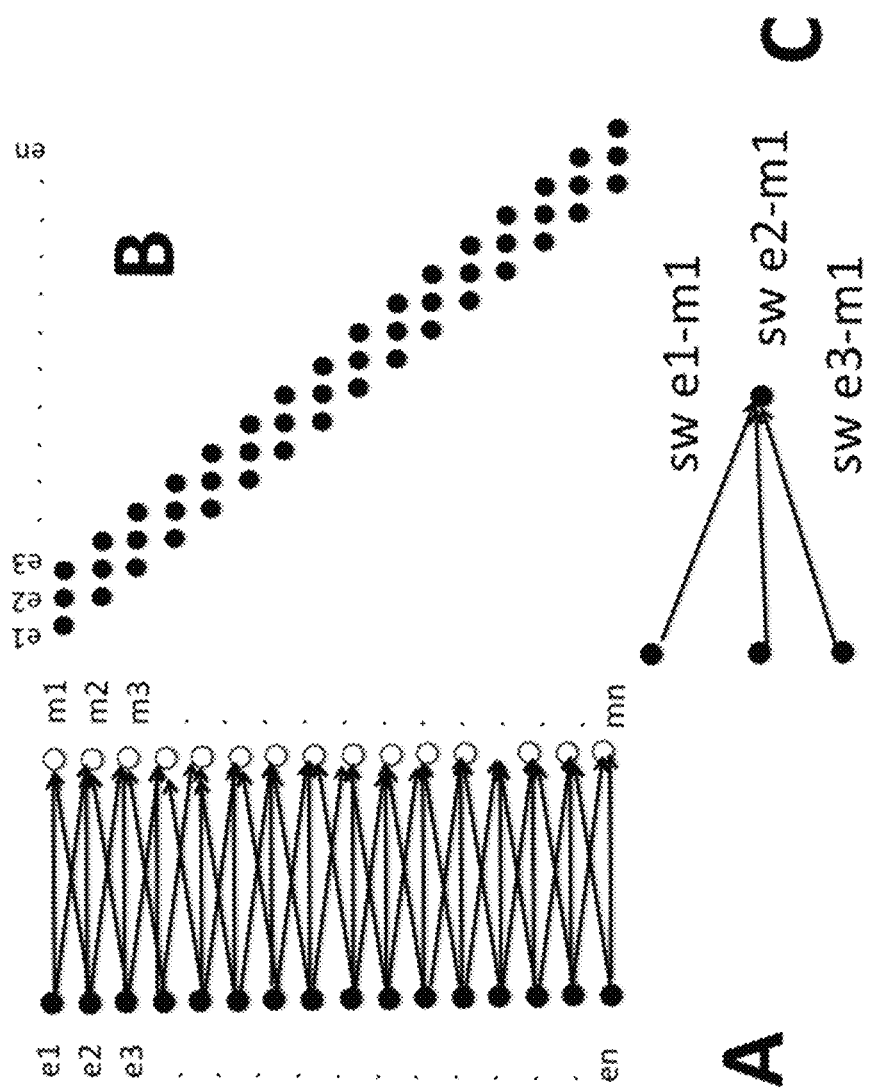
FIG. 8 shows a neural network for use in an algaebric deconvolution algorithm for determining distance of an electrode from a target.
Figure 9:
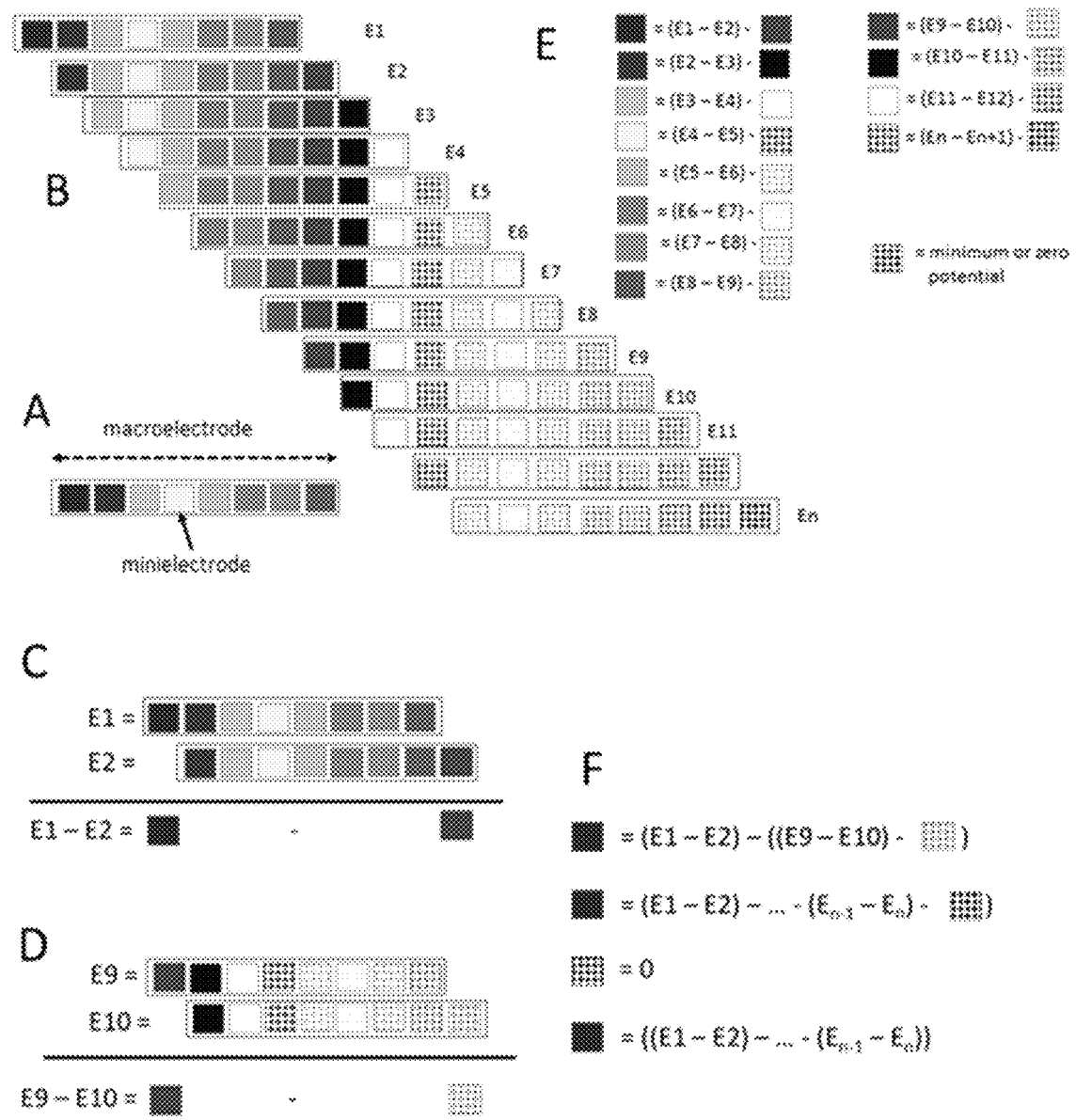
FIG. 9 shows that the macroelectrode (A) can be considered as a linear composite of "minielectrodes". Thus, the electrical potential on the entire macroelectrode can be considered as the sum of the potentials on the individual minielectrodes.

A deconvolution algorithm is applied to the sequence of evoked potentials for each type of stimuli and location of stimulus application. One method employed is the algebraic reconstruction technique (FIGS. 5, 8-10). The first approach, the algebraic reconstruction technique, can be applied to the electrical evoked potentials recorded in the electrode contact (FIGS. 8 and 9).

In one embodiment, the deconvolution is an algebraic reconstruction technique implemented using a two layer neural network (FIG. 8). The voltage recorded in the macroelectrode at single position can be considered as the sum of a series of voltages on "minielectrodes" as shown in FIG. 8-9. The problem to be solved is to calculate the voltages on the minielectrodes from data from the macroelectrode that is moved in an overlapping fashion through the trajectory. To accomplish this, a highly robust and efficient neural network approach (FIG. 8) can be used to perform the algebraic deconvolution. The network can consist of two layers. The first layer (FIG. 8, panel A) can have n number of neurons corresponding to the sequential minielectrodes determined by dividing the length of the intended trajectory by the distance the macroelectrode is moved. The second layer consists of a number neurons equal to the number of macroelectrode recording sites that equals the number of minielectrodes. Each minielectrode connects to and sums at the appropriate macroelectrode. The minielectrodes that connect to the macroelectrode are the minielectrodes of the trajectory occupied by the macroelectrode at each recording site. With reference to FIG. 8, panel B, the input values to the first layer contain the value of 1. The connection of each minielectrode to the appropriate macroelectrode can be modified by a synaptic weight (sw), where the value at the input to the second layer neuron is just 1 times the synaptic weight (sw). With reference to FIG. 8, panel C, the training vector will be the voltage recorded with the macroelectrode at each position in the trajectory. Initially the synaptic weights are assigned random values. The output of the second layer of neurons is compared to the measured macroelectrode values. Differences are considered error signal or vector that then are back propagated using the Generalized Delta Rule and the output of the second layer recalculated and compared to the measured macroelectrode values. The Generalized Delta Rule is a common tool for working with neural networks, see, e.g., McClelland. Training Hidden Units: The Generalized Delta Rule, in Parallel Distributed Processing Handbook. The resulting errors vector again is back propagated to create a new set of synaptic weights. This process continues re-iteratively until the error signal reaches a minimum. The synaptic weights at the final solution are then taken as the voltages on each of the minielectrodes.

With continuing reference to FIG. 8, each macroelectrode can be considered the combination of a sequence of minielectrodes. The voltage recorded on the macroelectrode equals the sum of the voltage on the minielectrodes. The task is to calculate the voltages on the minielectrode from the voltages measured from the macroelectrode. A series of macroelectrode recordings are made as the macroelectrode is advanced in small steps through the trajectory. Thus at each macroelectrode position, the minielectrodes associated with each macroelectrode will overlap except the first minielectrode of the preceding macroelectrode and the final minielectrode of the subsequent macroelectrode position. A first layer of neurons comprise the minielectrodes FIG. 8, panel A ($e_1$–$e_n$), which connect to neurons in the second layer representing the macroelectrode recording FIG. 8, panel A ($m_1$–$m_n$). The calculated macroelectrode voltage is considered the sum of the inputs from the associated minielectrodes which is the input value of the minielectrode (equal to 1) times the synaptic weight (sw) (FIG. 8, panel C).

On the first iteration, the values of the synaptic weights are randomize to some non-zero value. The set of calculated macroelectrode voltages are determined. The difference between the measured and calculated macroelectrode voltages create and error vector (on error value per position of the macroelectrode). The error vector is then used to modify the synaptic weights using the standard Back Propagation method and the Generalized Delta Rule. The calculated macroelectrode values are determined and compared to the measured voltages to create another error vector that again is used to recalculate the synaptic weights. This process is repeated until the error vector reaches a stable minimum. The synaptic weights are taken as the voltages on the minielectrodes and then used to determine the location of the source of the evoked potential as described below.

Stated another way, as a macroelectrode passes through a trajectory, each minielectrode ($e_n$) measures a voltage (potential) from the evoked potential. The distance that the macroelectrode moves results in sections of the macroelectrode that overlap with a subsequent (or previous) step in the trajectory, and sections of the macroelectrode that do not overlap. By continually advancing the macroelectrode, it is possible to determine the potential measured by each minielectrode by summing the potential of the overlapping regions (i.e. $e_2$-$e_9$ and $e_1$-$e_8$), and then identifying the difference therebetween (i.e. ($e_1$-$e_9$)–($e_2$-$e_8$)), which would leave $e_1$ and $e_9$. By assuming that the last minielectrode ($e_n$)=0, the voltage at each minielectrode can then be determined.

By knowing the voltage measured at each minielectrode (e), a curve can then be identified, whereby the voltage increases as the macroelectrode advances, and the voltage then falls off. For example, in a scenario, the maximum voltage could be detected at $e_5$. The result is that the user can know than e5 is the minielectrode closest to the critical/target area, or the source of the evoked potential. Note that the electrode must pass through a full trajectory to acquire sufficient information to determine distance to the source of an evoked potential. This trajectory may be pre-planned, for example as the result of a prior anatomical scan (magnetic resonance imaging, positron emission topography, computed tomography, or the like), or, the trajectory can be initiated without any prior information.

Figure 13:
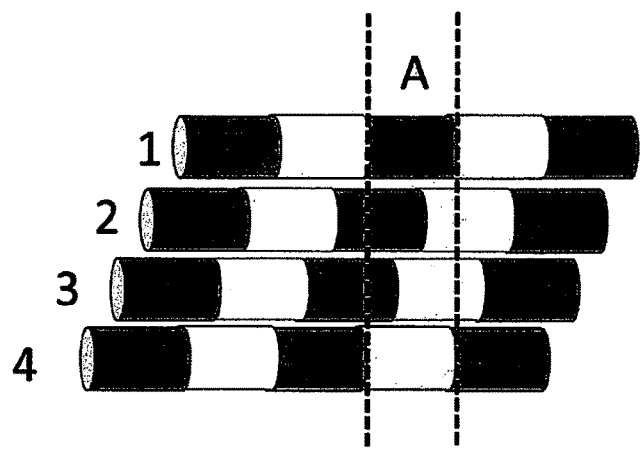
FIG. 13 shows an embodiment of a lead that holds a single macroelectrode that traverses the trajectory. Another embodiment holds a linear array of multiple leads each with one or more electrodes arranged such that the entire array needs only to move a distance equal to the gap between the macroelectrodes.
Figure 14:
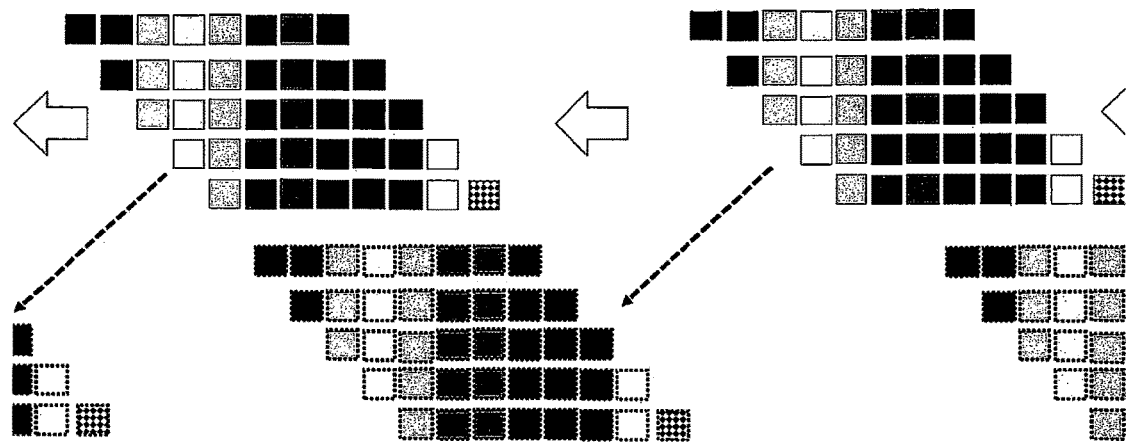
FIG. 14 shows a demonstration of how sets of macroelectrodes, each containing a set of virtual minielectrodes defined as the areas not overlapping in the sequence of movements, can be moved to the trajectory so as to create an entire set of minielectrodes needed for source localization.

FIGS. 13 and 14 further show the usefulness of a set of macroelectrodes, and how these macroelectrodes traverse the trajectory and the microscopic movement necessary to provide source localization. Thus, the electrical potential on the entire macroelectrode can be considered as the sum of the potentials on the individual minielectrodes. As the macroelectrode is advanced, in steps approximately equal to or equal to the length of a minielectrode, the composites of each macroelectrode overlap (shown in FIG. 9, panel B). The potentials of the macroelectrode on contiguous positions (C and D) can be subtracted and the result is equal to the potential first minielectrode of the first position minus the potential on the last minielectrode in the second position. As shown in (C), the potential difference between the first and second position is equal to the potential of the first minielectrode minus the potential on the $8^{th}$ minielectrode. The same approach can be taken with all of the minielectrodes (E). The potential on the $8^{th}$ minielectrode can be defined in terms of the difference in the electrical potential measured on the $9^{th}$ and $10^{th}$ macroelectrode positions and the potential on the $16^{th}$ minielectrode. Now the potential on the first minielectrode can determine the combination of potential differences between the $1^{st}$ and $2^{nd}$ macroelectrodes, the difference between the $9^{th}$ and $10^{th}$ macroelectrodes and the potential on the $16^{th}$ minielectrode (F).

Ultimately, every minipotential can be determined by combinations of differences in the electrical potential of the macroelectrode at each position and the last minielectrode. However, there is no way to calculate the potential on the last minielectrode. This problem can be circumvented by assuming that the last minielectrode is very far away from the source of the evoked potential, which is easily done by the user arbitrarily starting or ending the macroelectrode trajectory far from the general location of the anatomical/physiological structure. In this case the potential of the last minielectrode can be assumed to be equal to zero and consequently, the potential of any minielectrode can be determined. The minielectrode associated with the highest potential is in the plane of the source of the evoked potential orthogonal to the long axis of the macroelectrode.

At each point at which the LFP is sampled, the evoked potential will be some integral of the electrical fields over the entire contact. The electrode is then advanced over a small step and the evoked potential resampled. Again, the evoked potential will be some integral of the electrical field. However, the evoked potential will share some of the same information as the previous evoked potential. Thus, the length of the two samples that overlap share the same electrical field while the non-overlapping length does not. The potential recorded on the electrode at any one location can be considered as the sum of smaller electrical potentials across the length of the electrode as described by the equation in FIG. 9 or as shown above in discussion of the Radon transform and as shown below in the discussion of the trigonometric functions. Thus, each recording that is offset by a small set results in a series of simultaneous algebraic equations. Also, the segments that are overlapping have the same potential. This results in another set of equations that then allow solution of the simultaneous equations.

With further reference to FIG. 9, in an embodiment an explicit algebraic reconstruction technique can be applied to the electrical evoked potentials recorded in the electrode contact (FIG. 9). At each point at which the LFP is sampled, the evoked potential will be some integral of the electrical fields over the entire contact. The electrode is then advanced over a small step and the evoke potential resampled. Again, the evoked potential will be some integral of the electrical field. However, the evoked potential will share some of the same information as the previous evoked potential. Thus, the length of the two samples that overlap share the same electrical field while the non-overlaping length does not. The potential recorded on the electrode at any one location can be considered as the sum of smaller electrical potentials across the length of the electrode as described by the equation in FIG. 9. Thus, each recording that is offset by a small set results in a series simultaneous algebraic equations. Also, the segments that are overlapping have the same potential. This results in another set of equations that then allow solution of the simultaneous equations.

The deconvolution algorithm can be implemented using computer system (7), having appropriate processing mechanisms and computer-readable media for storing and executing computer-readable instructions, such as programming instructions, code, and the like. Personal computers in a computing system environment can be provided. This computing system environment can include, but is not limited to, at least one computer having certain components for appropriate operation, execution of code, and creation and communication of data. For example, the computer includes a processing unit (typically referred to as a central processing unit or CPU) that serves to execute computer-based instructions received in the appropriate data form and format. Further, this processing unit can be in the form of multiple processors executing code in series, in parallel, or in any other manner for appropriate implementation of the computer-based instructions.

In order to facilitate appropriate data communication and processing information between the various components of the computer, a system bus can be utilized. The system bus can be any of several types of bus structures, including a memory bus or memory controller, a peripheral bus, or a local bus using any of a variety of bus architectures. In particular, the system bus facilitates data and information communication between the various components (whether internal or external to the computer) through a variety of interfaces, as discussed hereinafter.

The computer can include a variety of discrete computer-readable media components. For example, this computer-readable media can include any media that can be accessed by the computer, such as volatile media, non-volatile media, removable media, non-removable media, etc. As a further example, this computer-readable media can include computer storage media, such as media implemented in any method or technology for storage of information, such as computer-readable instructions, data structures, program modules, or other data, random access memory (RAM), read only memory (ROM), electrically erasable programmable read only memory (EEPROM), flash memory, or other memory technology, CD-ROM, digital versatile disks (DVDs), or other optical disk storage, magnetic cassettes, magnetic tape, magnetic disk storage, or other magnetic storage devices, or any other medium which can be used to store the desired information and which can be accessed by the computer. Further, this computer-readable media can include communications media, such as computer-readable instructions, data structures, program modules, or other data in a modulated data signal, such as a carrier wave or other transport mechanism and include any information delivery media, wired media (such as a wired network and a direct-wired connection), and wireless media (such as acoustic signals, radio frequency signals, optical signals, infrared signals, biometric signals, bar code signals, etc.). Of course, combinations of any of the above are included within the scope of computer-readable media.

The computer further includes a system memory with computer storage media in the form of volatile and non-volatile memory, such as ROM and RAM. A basic input/output system (BIOS), with appropriate computer-based routines, assists in transferring information between components within the computer and is normally stored in ROM. The RAM portion of the system memory typically contains data and program modules that are immediately accessible to or presently being operated on by a processing unit, e.g., an operating system, application programming interfaces, application programs, program modules, program data, and other instruction-based computer-readable codes.

The computer can also include other removable or non-removable, volatile or non-volatile computer storage media products. For example, the computer can include a non-removable memory interface that communicates with and controls a hard disk drive, i.e., a non-removable, non-volatile magnetic medium; and a removable, non-volatile memory interface that communicates with and controls a magnetic disk drive unit (which reads from and writes to a removable, non-volatile magnetic disk); an optical disk drive unit (which reads from and writes to a removable, non-volatile optical disk, such as a CD ROM); a Universal Serial Bus (USB) port for use in connection with a removable memory card, etc. However, it is envisioned that other removable or non-removable, volatile or non-volatile computer storage media can be used in the exemplary computing system environment, including, but not limited to, magnetic tape cassettes, DVDs, digital video tape, solid state RAM, solid state ROM, etc. These various removable or non-removable, volatile or non-volatile magnetic media are in communication with the processing unit and other components of the computer via the system bus. The drives and their associated computer storage media discussed above provide storage of operating systems, computer-readable instructions, application programs, data structures, program modules, program data, and other instruction-based computer-readable code for the computer (whether duplicative or not of this information and data in the system memory).

A user can enter commands, information, and data into the computer through certain attachable or operable input devices, such as a keyboard, a mouse, etc., via a user input interface. Of course, a variety of such input devices can be utilized, e.g., a microphone, a trackball, a joystick, a touch-pad, a touch-screen, a scanner, etc., including any arrangement that facilitates the input of data and information to the computer from an outside source. As discussed, these and other input devices are often connected to the processing unit through the user input interface coupled to the system bus but can be connected by other interface and bus structures, such as a parallel port, game port, or a universal serial bus (USB). Still further, data and information can be presented or provided to a user in an intelligible form or format through certain output devices, such as a monitor (to visually display this information and data in electronic form), a printer (to physically display this information and data in print form), a speaker (to audibly present this information and data in audible form), etc. All of these devices are in communication with the computer through an output interface coupled to the system bus. It is envisioned that any such peripheral output devices can be used to provide information and data to the user.

The computer can operate in a network environment through the use of a communications device, which is integral to the computer or remote therefrom. This communications device is operable by and in communication with the other components of the computer through a communications interface. Using such an arrangement, the computer can connect with or otherwise communicate with one or more remote computers, such as a remote computer, which can be a personal computer, a server, a router, a network personal computer, a peer device, or other common network nodes, and typically includes many or all of the components described above in connection with the computer. Using appropriate communication devices, e.g., a modem, a network interface or adapter, etc., the computer can operate within and communicate through a local area network (LAN) and a wide area network (WAN), but can also include other networks such as a virtual private network (VPN), an office network, an enterprise network, an intranet, the Internet, etc. It will be appreciated that the network connections shown are exemplary and other means of establishing a communications link between the computers can be used.

As used herein, the computer includes or is operable to execute appropriate custom-designed or conventional software to perform and implement the processing steps of the method and system of the present invention, thereby forming a specialized and particular computing system. Accordingly, the presently-invented method and system can include one or more computers or similar computing devices having a computer-readable storage medium capable of storing computer-readable program code or instructions that causes the processing unit to execute, configure, or otherwise implement the methods, processes, and transformational data manipulations discussed hereinafter in connection with the present invention. Still further, the computer can be in the form of a personal computer, a personal digital assistant, a portable computer, a laptop, a palmtop, a mobile device, a mobile telephone, a server, or any other type of computing device having the necessary processing hardware to appropriately process data to effectively implement the presently-invented computer-implemented method and system.

Figure 10:
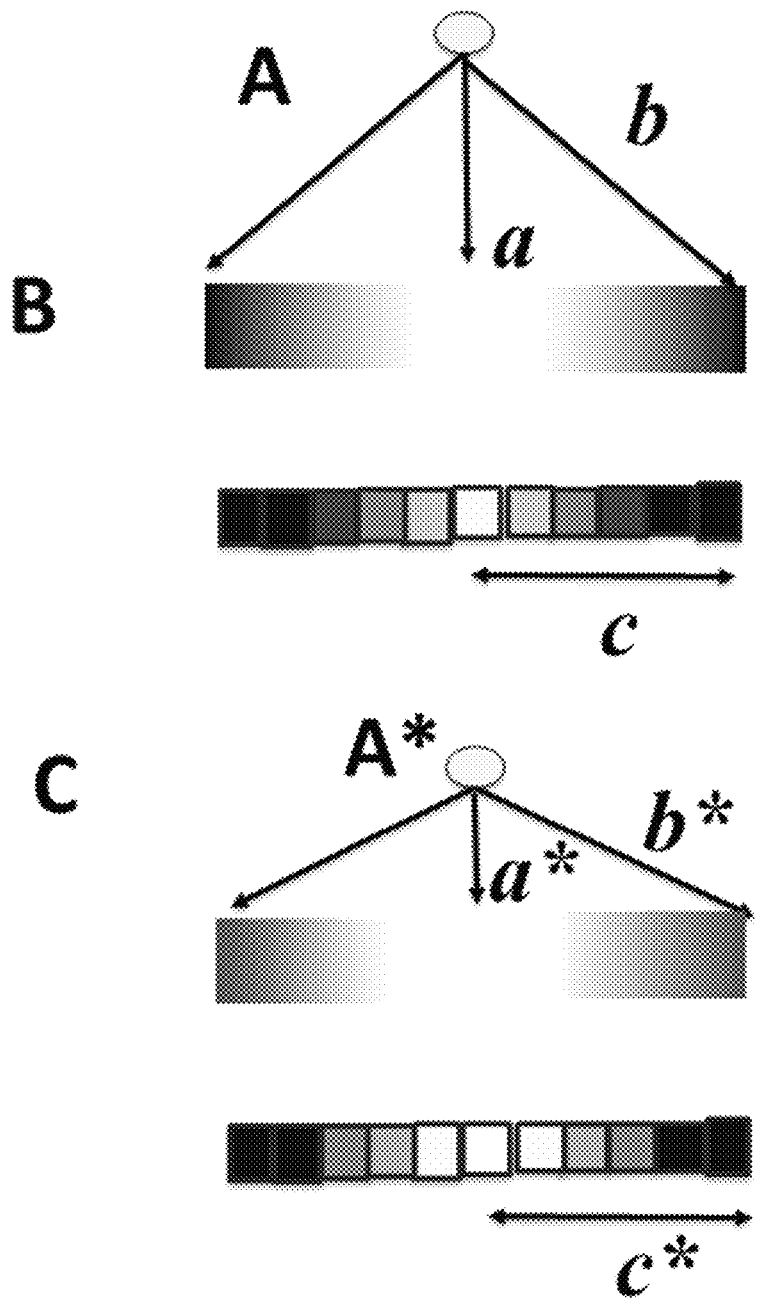
FIG. 10 shows a schematic representation of a method to determine the distance of the signal source to the electrode according to one embodiment of the present invention.

The method described above and as shown for example in FIGS. 8-10 can be used to estimate the distance of the signal source to the electrode. It is based on the concept that the closer of the signal source to the electrode the greater is the potential gradients over the series of electrode positions (FIG. 10). As shown in FIG. 10, the partitioning produces a gradient (c and c*). The next step is to estimate the distance of the signal source to the electrode. The intensity of any partition is proportional to the distance between the electrode and the signal source. The gradient is the difference in the potentials at each end of the gradient which in turn is proportional to the difference between the signal source and the electrode and is proportional to a:b when the signal source is farther away (B) compared to a*:b* as shown in C; a:b≥a*:b*.

As shown by the derivations below, the distance of the point source to the macroelectrode trajectory can be determined without having to know the absolute voltage at the source. Rather, only the voltage at the minielectrode with the maximum potential compared to the voltage at any other minielectrode at known distances from the minielectrode with the maximum voltage.

Returning to the above description of determining the potential sensed at each minielectrode (e) (FIGS. 8-10), knowledge of the minielectrode sensing the maximum potential is key, but does not inform the user as to the distance from that minielectrode to the target/source of evoked potential. Thus, the system must determine the distance (r) of the point source of the local field potential from the trajectory of the macroelectrode. The exact voltage of the point source ($V_s$) cannot be known. However, the distance can be determined by the fall-off of the voltages in the minielectrodes ($V_x$) on each side of the minielectrode with the maximum voltage ($V_0$) (FIG. 10). Thus, the distance to the local field potential source can be determined by the fall off of the voltages from the maximum without knowledge of the actual voltage of the local field potential. The following derivation demonstrates this method. The approach is based on the trigonometric function and the principle that the electrical field potential (V) falls off with the radius (V≈1/r). Following are derivations of the V as a function of the distance of the source to the "minielectrodes". The "minielectrode" closest to the source will have a potential $V_0$ which equals the voltage at the source ($V_s$) divided by the distance r from the "minielectrode" with the maximal voltage. Any other "minielectrode" will experience a voltage ($V_x$) as a function of the square root of the square of the distance, r, and the square of the distance of the "minielectrode", $d_x$, to the "minielectrode" associated with the maximal voltage.

$$V_0 = V_s/r \qquad \text{Eq. 1}$$

$$V_0 * r = V_s \qquad \text{Eq. 2}$$

$$V_x = V_s/(r^2 + d_x^2)^{1/2}$$

$$V_x^2 = V_s^2/(r^2 + d_x^2)$$

$$(r^2 + d_x^2)V_x^2 = V_0^2 * r^2 \qquad \text{Eq. 3}$$

$$r^2 + d_x^2 = (V_0^2 * r^2)/V_x^2$$

$$r^2 + d_x^2 = (V_0^2 * r^2)*(1/V_x^2)$$

$$r^2/(V_0^2 * r^2) + d_x^2/(V_0^2 * r^2) = 1/V_x^2$$

$$1/V_0^2 + d_x^2/(V_0^2 * r^2) = (1/V_x^2)$$

$$1/V_0^2 + (d_x^2/V_0^2)*r^2) = (1/V_x^2)$$

$$d_x^2/V_0^2 * r^2) = 1/V_x^2 - 1/V_0^2$$

$$r^2 = (V_0^2/d_x^2)(1/V_x^2 - 1/V_0^2)$$

$$r^2 = (V_0^2/d_x^2 * V_x^2) - (V_0^2/d_x^2 * V_0^2)$$

$$r^2 = (V_0^2/d_x^2 * V_x^2) - (1/d_x^2)$$

$$d_x^2 * r^2 = V_0^2/V_x^2 - 1$$

$$r = ((V_0^2/V_x^2 - 1)^{1/2})/d_x \qquad \text{Eq. 4}$$

The result of the derivations is that the distance r can be computed from $V_0$ (minielectrode sensing maximum voltage) and $V_x$ (voltage at each minielectrode (1–n)), which are measurable, and distance that the macroelectrode moves, $d_x$, which is known (Eq. 4). Note, the source $V_s$ does not need to be known and actually can be any value in the present method. This obviates and overcomes prior difficulties of having to measure or know the source voltage $V_s$. The above derivation allows for precise distances to be calculated without ever needing to know the voltage at the source of the evoked potential. Rather, buy knowing the maximum sensed voltage by a minielectrode, the voltage sensed by each minielectrode, and the distance moved by the macroelectrode, one can determine the distance to the source, and thus avoid a critical brain structure.

The distance r can then be compared to a predetermined threshold value, which comparison informs the user and/or instructs the computer program to advance the electrode further, or to stop progression of the electrode through tissue. The precise value for the threshold value, which can be denoted 'Y', can be described as the evoked potential for a structure in which stimulation would produce adverse effects is greater than the radius of the volume of tissue activation anticipated from the purposeful stimulation, and less than the radius of the volume of tissue activation for structures whose stimulation would produce a beneficial effect. For example, and without limitation, for DBS the current volume of tissue activation has a radius of 2-3 mm. However, those of skill in the art will appreciate that this threshold value 'Y' can be adjusted based on brain structure, and can range from 1-5 mm, with all subranges therebetween inclusive therein, in increments of 0.1 mm (that is, including 1.1-4.9, 1.2-4.8, etc.).

At the completion (end) of a macroelectrode, the invention will determine whether the specific physiological targets are detected and, if so, the distance and direction the targets are relative to the macroelectrode, including but not limited to the DBS lead. Thus, the user will be able to determine if the current trajectory is appropriate for implantation of the therapeutic device or agent and, if not, in which direction targeting should continue.

Figure 11:
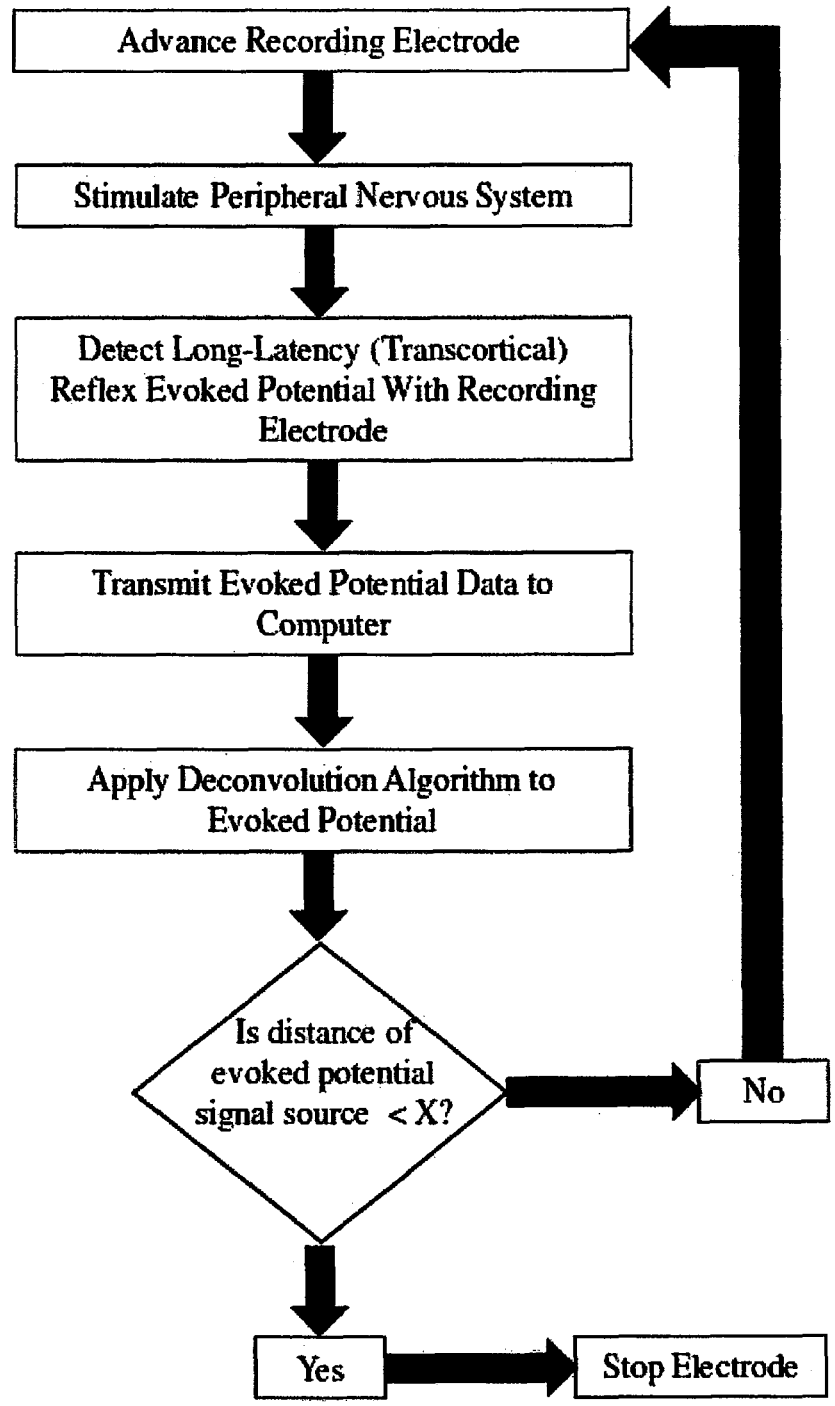
FIG. 11 shows a flowchart of a method according to one embodiment of the present invention.

With reference to FIG. 11, depicted therein is a method according to one embodiment of the present invention. The method includes the steps of advancing a recording electrode and stimulating the peripheral nervous system via one of the sensory modalities described previously herein. For example, the electrode can be advanced in any suitable, safe, distance per unit of time, for example at the determination of the user, in step lengths chosen by the user. A typical speed of advancement can be 0.01 mm/s with step lengths of 0.01 mm, however those of skill in the art will understand and appreciate that speed can be adjusted based on results of the deconvolution or reconstruction algorithm (i.e., faster advancement when a critical structure is known to be far from the electrode, slower as such distance decreases), to range from 0.001 mm/s to 0.1 mm/s, with steps of any range falling therein.

As the recording electrode is advanced, and peripheral stimulation is applied, evoked potentials are measured by the electrode and the evoked potential is transmitted to the interface and/or computing system. The computer, having media for implementing deconvolution algorithm(s), such as those described above and in FIGS. 8-10, and/or Radon transforms, determines distance from the electrode to the source of the evoked potential signal, and determines whether the electrode should be further advanced by the drive. If the signal source is sufficiently far from the electrode (that is, critical cortical/subcortical structures and areas that must be avoided during, for example, DBS are not in the vicinity of the electrode), then the computer system will allow/instruct the drive to advance the electrode further. If the computer, based on signal source, determines that advancement of the electrode should cease, a signal to do so will be communicated to the drive/electrode (or an advancement signal will not be supplied to the drive/electrode). In some embodiments, the surgeon will be equipped with an operator presence control or vigilance control (a so-called "dead man's switch"), whereby the electrode can advance while a certain pressure or input is provided by a human operator, but if said input is denied, advancement will not continue.

While FIG. 11 depicts the steps of the method occurring sequentially, those of skill will understand that advancement, stimulation, detection, and decision-making can occur simultaneously, or near-simultaneously, to increase speed or electrode placement/path planning, while maintaining the required precision and accuracy needed for placement of medical devices within, for example and without limitation, the brain of a patient.

On a practical level, the software that enables the computer system to perform the operations described above, for example, the deconvolution and/or Radon transforms (derivations or otherwise), can be supplied on any one of a variety of media. Furthermore, the actual implementation of the approach and operations of the invention are actually statements written in a programming language. Such programming language statements, when executed by a computer, cause the computer to act in accordance with the particular content of the statements. Furthermore, the software that enables a computer system to act in accordance with the invention can be provided in any number of forms including, but not limited to, original source code, assembly code, object code, machine language, compressed or encrypted versions of the foregoing, and any and all equivalents.

One of ordinary skill in the art will appreciate that "media", or "computer-readable media", or "non-transitory computer readable media", as used herein, can include a diskette, a tape, a compact disc, an integrated circuit, a ROM, a CD, a cartridge, a remote transmission via a communications circuit, or any other similar medium useable by computers now known or hereafter developed. For example, to supply software for enabling a computer system to operate in accordance with the invention, the supplier might provide a diskette or might transmit the software in some form via satellite transmission, via a direct telephone link, or via the Internet. Thus, the term, "computer readable medium" is intended to include all of the foregoing and any other medium by which software can be provided to a computer.

Although the enabling software might be "written on" a diskette, "stored in" an integrated circuit, or "carried over" a communications circuit, it will be appreciated that, for the purposes of this application, the computer useable medium will be referred to as "including" the software. Thus, the term, "including" is intended to encompass the above and all equivalent ways in which software is associated with a computer usable medium. For the sake of simplicity, therefor, the term "program product" is used to refer to a computer useable medium, as defined above, which includes any form of software to enable a computer system to operate according to the above-identified invention. Thus, the invention is also embodied in a program product including software instructions which enable a computer or computers to analyze evoked potentials with a region of the body according to the invention.

While the foregoing drawings and descriptions set forth functional aspects of the disclosed systems, no particular arrangement of software for implementing these functional aspects should be inferred from these descriptions unless explicitly stated or otherwise clear from the context. Similarly, it will be appreciated that the various steps identified and described above can be varied, and that the order of steps can be adapted to particular applications of the techniques disclosed herein. All such variations and modifications are intended to fall within the scope of this disclosure. As such, the depiction and/or description of an order for various steps should not be understood to require a particular order of execution for those steps, unless required by a particular application, or explicitly stated or otherwise clear from the context.

The methods and/or processes described above, and steps thereof, can be realized in hardware, software, or any combination of hardware and software suitable for a particular application. The hardware can include a general purpose computer and/or dedicated computing device or specific computing device or particular aspect or component of a specific computing device. The processes can be realized in one or more microprocessors, microcontrollers, embedded microcontrollers, programmable digital signal processors, or other programmable devices, along with internal and/or external memory. The processes can also, or instead, be embodied in an application specific integrated circuit, a programmable gate array, a programmable array logic, or any other device or combination of devices that can be configured to process electronic signals. It will further be appreciated that one or more of the processes can be realized as a computer executable code capable of being executed on a machine readable medium.

The computer executable code can be created using a structured programming language such as C, C#, C+, Fortran, basic, Pascal, assembly, or machine code, an object oriented programming language such as C++, or any other high-level or low-level programming language (including assembly languages, hardware description languages, and database programming languages and technologies) that can be stored, compiled, or interpreted to run on one of the above devices, as well as heterogeneous combinations of processors, processor architectures, or combinations of different hardware and software, or any other machine capable of executing program instructions.

Thus, in one aspect, each method described above and combinations thereof can be embodied in computer executable code that, when executing on one or more computing devices, performs the steps thereof. In another aspect, the methods can be embodied in systems that perform the steps thereof, and can be distributed across devices in a number of ways, or all of the functionality can be integrated into a dedicated, standalone device or other hardware. In another aspect, the means for performing the steps associated with the processes described above can include any of the hardware and/or software described above. All such permutations and combinations are intended to fall within the scope of the present disclosure.

In addition to the methods of locating an electrode and methods of planning or routing surgery, also included in the present invention is a method of performing spinal surgery on a patient in need thereof. The spinal surgery can be any type of surgery where there is even a slight risk of impinging on the spinal column or spinal cord of a patient. For example, and without limitation, such a method will be understood by those of ordinary skill in the art to be valuable in spinal fusion surgeries, laminectomies, foraminotomies, disectomies, disc replacements, intralaminar implantations, and the like. As used herein, the term "spinal column" means the vertebral column, or the collection of vertebral bones that enclose or house the spinal cord. As used herein, the term "spinal cord" means the collection of nerves and support cells that lie within the spinal or vertebral column.

Figure 12:
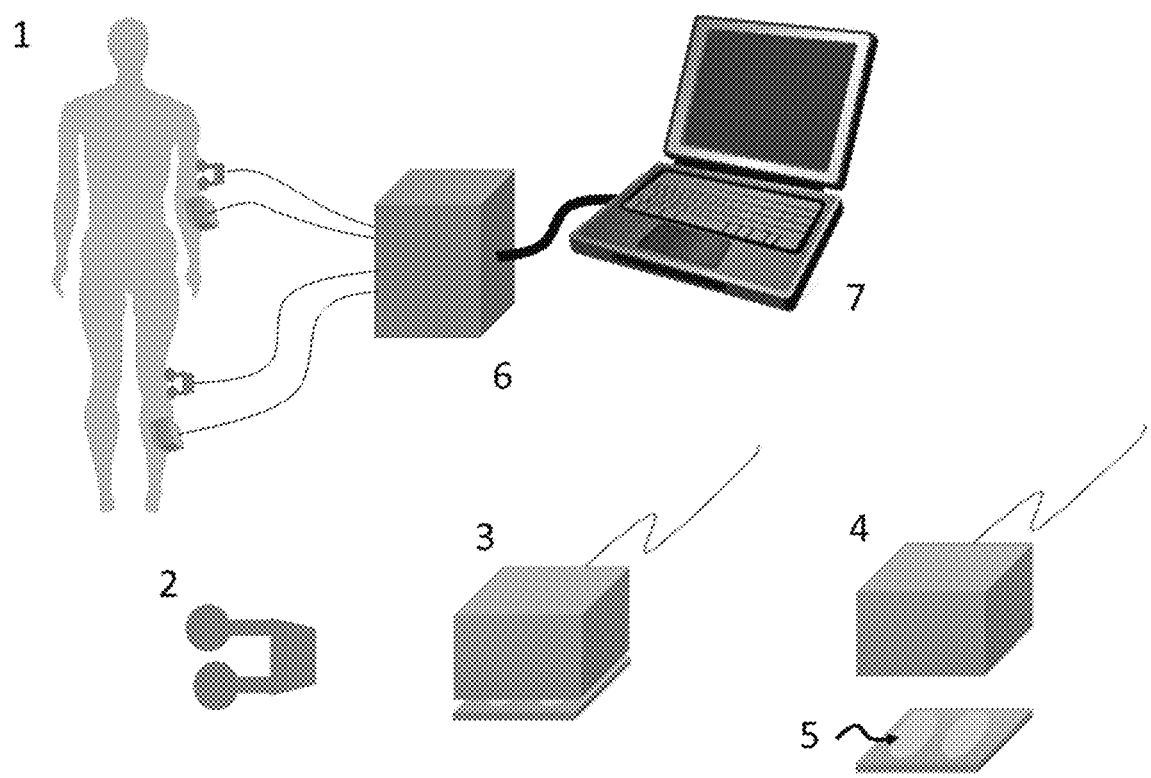
FIG. 12 shows a schematic of a system for use in spinal surgery according to one embodiment of the present invention.

In an embodiment, the method of performing spinal surgery utilizes the principles described in detail herein, for example and without limitation, use of long latency transcortical reflexes to determine and confirm the integrity of the spinal cord. An embodiment of the method and a system therefore is shown in FIG. 12, which shows a schematic representation of a possible system for such surgery. As shown in FIG. 12, electrodes to stimulate a peripheral nerve (2) and a combined device (3) including a mechanical stimulator/vibrator (4) and surface electrodes (5) for recording the electromyographic responses to the peripheral nerve stimulation.

In some embodiments, the method includes the steps of stimulating a peripheral muscle. This stimulation can be accomplished by use of a mechanical stimulator, such as a vibrating device. Devices for providing mechanical stimulation are known to those of skill in the art, and are widely available from commercial sources. In non-limiting embodiments, the vibrator/mechanical device is used to stimulate an extremity, such as a portion of the arm or leg of a patient. Stimulation can be of any duration and strength suitable to evoke a field potential within the region of interest for the surgeon. In non-limiting embodiments, the stimulation occurs for tens of milliseconds to tens of seconds with a 1-5 mm amplitude, and frequencies from 20 Hz to 220 Hz.

The method further includes the step of detecting a long latency transcortical reflex through use of electromyography electrodes (5). Both the stimulating devices (2, 4) and the measuring electrode (5) can be in communication, wireless or otherwise, with computer system (7). As described above, this communication can be wired (i.e., the measuring/recording electrode (5) and/or the stimulating devices (2, 4)) can be hard wired or directly connected to the computer (7), or the communication between the measuring/recording electrode (5) (and/or the stimulating devices (2, 4)) and the computer (7) can be wireless, for example by WLAN or other wireless protocols and methods, by Bluetooth, ZigBee, EnOcean, TransferJet, Wireless USB, and the like known to those of skill in the art. Those of skill in the art will appreciate that wireless communication between devices is possible for transmission of recorded data from recording/measuring electrode (5) to computer system (7) and, in some embodiments, of instructions from computer system (7) to stimulating devices (2, 4).

In some embodiments, in addition to mechanical stimulation of a muscles, the method also includes concurrent, or near-concurrent, stimulation of a nerve or nerve bundle innervating or receiving information from the muscle that is stimulated. For example, and without limitation, the combination vibrator/electrodes can be placed over the flexor carpi ulnaris and the peripheral nerve stimulating electrodes over the ulnar nerve just behind the medial epicondyle at the elbow.

In some embodiments, an interface (6) can be included with the system useful for the method of spinal surgery described herein, which interface (6) can provide communication between the measuring/recording electrode (5) and/or the stimulating devices (2, 4) and computer system (7). The computer system (7) and/or interface (6) can include an amplifier for amplifying the signal detected by electrode (5). Amplifiers are known to those of skill in the art, and are obtainable from numerous commercial sources, for example from Grass Technologies (Warwick, R.I. USA), FHC, Inc. (Bowdoin, Me. USA), AlphaOmega Co. USA, Inc. (Alpharetta, Ga. USA), and Medtronic, Inc. (Minneapolis, Minn. USA).

In other non-limiting embodiments, the interface (6) includes one or more filters known to those of skill in the art for filtering electrical signals of field and evoked potentials. As is understood by those of skill in the art, filters are often included in the amplifier, such as those identified herein. Filters useful in the present system and method can be, for example and without limitation, band-pass filters. The blocking setting of the band-pass filter can be set to any useful threshold or range suitable for maximizing clarity of received data from electrode (5). While typical filter setting can be in the range of 500 Hz (high pass) and 24 k Hz (low pass), those of skill in the art will appreciate and understand that those settings can be adjusted to provide the clearest signal possible.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A method of determining a distance to a target in a patient, comprising:
   stimulating for a first time, with a stimulating device, the patient's peripheral nervous system;
   recording, using a macroelectrode recording electrode inserted within a region of interest in the patient, a field potential evoked from the first stimulation;
   calculating, using at least one processor, the evoked potential from the first stimulation;
   advancing, with a drive, the macroelectrode recording electrode along a trajectory;
   stimulating for a second time, with the stimulating device, the patient's peripheral nervous system;
   recording, using the macroelectrode recording electrode, a field potential evoked from the second stimulation;
   calculating, using at least one processor, the evoked potential from the second stimulation;
   determining, using at least one processor and based at least on the evoked potential from the first stimulation and the evoked potential from the second stimulation, a position along a path travelled by the macroelectrode recording electrode corresponding to a largest evoked potential;
   determining, using at least one processor, a distance r from the position along the macroelectrode recording electrode path corresponding to the largest evoked potential to a source of the largest evoked potential in a plane orthogonal to a long axis of the macroelectrode; and
   determining, using at least one processor, whether r is less than a predetermined threshold Y, and wherein the predetermined threshold Y is a radius of an effective volume of tissue activation with an intended therapeutic brain stimulation for an intended target of the brain stimulation.

2. The method according to claim 1, wherein the stimulation is mechanical.

3. The method according to claim 1, wherein the stimulation is electrical.

4. The method according to claim 1, wherein the stimulation is mechanical and visual.

5. The method according to claim 1, wherein the step of determining the distance r is accomplished using a Radon transform or variation thereof.

6. The method according to claim 1, wherein the macroelectrode recording electrode is a segmented lead electrode.

7. The method according to claim 6, wherein the distance r is calculated using an equation $r=((V_0^2/V_x^2-1)^{1/2})/d_x$, wherein $V_0$ is a potential at an electrode recording the largest evoked potential, $V_x$ is a potential at any other electrode, and $d_x$ is a distance from the electrode having the potential $V_0$ and the electrode having the potential $V_x$.

8. The method of claim 1, wherein the macroelectrode recording electrode is a single lead macroelectrode.

9. A system comprising:
   a macroelectrode recording electrode and drive;
   at least one stimulator;
   at least one processor in communication with the macroelectrode recording electrode and the at least one stimulator; and
   a non-transitory computer readable medium in communication with the at least one processor and having one or more computer programs stored thereon that when executed by the at least one processor cause the system to perform the operations of:
      stimulating for a first time, with the at least one stimulator, a patient's peripheral nervous system;
      recording, with the macroelectrode recording electrode, a field potential evoked from the first stimulation;
      calculating the evoked potential from the first stimulation;
      advancing, by controlling the drive, the macroelectrode recording electrode;
      stimulating for a second time, with the at least one stimulator, the patient's peripheral nervous system;
      recording, with the macroelectrode recording electrode, a field potential evoked from the second stimulation;
      calculating the evoked potential from the second stimulation;
      determining, based at least in part on the field potential evoked from the first stimulation and the field potential evoked from the second stimulation, a distance r from the macroelectrode recording electrode to a source of a largest evoked potential in a plane orthogonal to a long axis of the macroelectrode;
      determining whether r is less than a predetermined threshold Y; and
   wherein the predetermined threshold Y is a radius of an effective volume of tissue activation with an intended therapeutic brain stimulation for an intended target of the brain stimulation.

10. The system according to claim 9, wherein the stimulator is a mechanical stimulator.

11. The system according to claim 9, wherein the stimulator is an electrical stimulator.

12. The system according to claim 9, wherein the stimulator comprises a mechanical stimulator and a visual stimulator.

13. The system according to claim 9, wherein the step of determining the distance r is accomplished using a Radon transform or variation thereof.

14. The system according to claim 9, wherein the macroelectrode recording electrode is a segmented lead electrode.

15. The system according to claim 14, wherein the distance r is calculated using an equation $r=((V_0^2/V_x^2-1)^{1/2})/d_x$, wherein $V_0$ is a potential at an electrode recording the largest evoked potential, $V_x$ is a potential at any other electrode, and $d_x$ is a distance from the electrode having the potential $V_0$ and the electrode having the potential $V_x$.

16. A method of planning a trajectory for an implantable medical device in a brain of a patient, comprising:
   inserting a macroelectrode recording electrode within a portion of the patient's central nervous system;
   stimulating the patient's peripheral nervous system and the patient's visual system;
   recording first evoked potential data within the patient's brain using the macroelectrode recording electrode;
   stimulating, for a second time, the patient's peripheral nervous system and the patient's visual system;

recording second evoked potential data with the patient's brain using the macroelectrode recording electrode;

applying, using at least one processor, a deconvolution algorithim to the first and second evoked potential data to determine a distance from the macroelectrode recording electrode to a source of evoked potential in a plane orthogonal to a long axis of the macroelectrode recording electrode; and determining, using at least one processor, whether the distance is greater than or less than a threshold, wherein the threshold is a radius of an effective volume of tissue activation with an intended therapeutic brain stimulation for an intended target of the brain stimulation.

17. A system comprising:

a macroelectrode recording electrode;

a drive configured to move the macroelectrode recording electrode;

at least one stimulator;

at least one processor in communication with the macroelectrode recording electrode, the drive, and the at least one stimulator; and a non-transitory computer readable medium in communication with the at least one processor and having one or more computer programs stored thereon that when executed by the at least one processor cause the system to perform the operations of:

recording, with the macroelectrode recording electrode, a first field potential evoked from a first stimulation of a patient's peripheral nervous system;

calculating a first evoked potential from the first stimulation;

advancing, with the drive, the macroelectrode recording electrode;

recording, with the macroelectrode recording electrode, a second field potential evoked from a second stimulation of the patient's peripheral nervous system;

calculating a second evoked potential from the second stimulation;

determining, based on at least the first evoked potential and the second evoked potential, a distance r from the macroelectrode recording electrode to a source a largest evoked potential in a plane orthogonal to a long axis of the macroelectrode;

determining whether r is less than a predetermined threshold Y, and wherein the predetermined threshold Y is a radius of an effective volume of tissue activation with an intended therapeutic brain stimulation for an intended target of the brain stimulation.

* * * * *

UNITED STATES PATENT AND TRADEMARK OFFICE
CERTIFICATE OF CORRECTION

PATENT NO. : 10,478,616 B2
APPLICATION NO. : 14/831495
DATED : November 19, 2019
INVENTOR(S) : Erwin B. Montgomery, Jr. et al.

It is certified that error appears in the above-identified patent and that said Letters Patent is hereby corrected as shown below:

In the Claims

Column 28, Line 1, Claim 9, delete "system" and insert -- system, --

Column 29, Line 4, Claim 16, delete "algorithim" and insert -- algorithm --

Column 30, Line 16, Claim 17, delete "source" and insert -- source of --

Signed and Sealed this
Tenth Day of March, 2020

Andrei Iancu
*Director of the United States Patent and Trademark Office*